United States Patent [19]

Lee

[11] Patent Number: 4,892,870

[45] Date of Patent: Jan. 9, 1990

[54] OXAZA HETEROCYCLES AND PHARMACEUTICAL COMPOSITIONS CONTAINING SAME

[75] Inventor: Sung J. Lee, Clarks Summit, Pa.

[73] Assignee: Biofor, Ltd., Waverley, Pa.

[21] Appl. No.: 227,572

[22] Filed: Aug. 1, 1988

[51] Int. Cl.$^4$ .................. C07D 267/04; A61K 31/55; A61K 31/695; C07F 7/08

[52] U.S. Cl. ..................... 514/211; 514/63; 514/230.8; 514/380; 540/487; 540/488; 544/63; 544/69; 548/243; 548/110

[58] Field of Search ....................... 514/63, 230.8, 211, 514/380; 540/487, 488; 544/63, 69; 548/243, 110

[56] References Cited

U.S. PATENT DOCUMENTS 4,552,585  11/1985  Chang ................................. 544/63

*Primary Examiner*—Robert T. Bond
*Attorney, Agent, or Firm*—Joseph W. Molasky & Assoc.

[57] ABSTRACT

A novel class of 5, 6 or 7 member heterocycles which belong to the 3-isoxazolidinone, 2H-1,2-oxazin-3 (4H)-one and 3-isoxazepinone series of compounds and which are substituted at the 4-carbon by a benzylidene radical. The compounds have utility as analgesic agents, immunomodulating agents, anti-inflammatory agents and anti-pyretic agents and they may be combined with excipients to provide formuations which are useful in treating arthritis and conditions generally associated with that disease.

44 Claims, No Drawings

OXAZA HETEROCYCLES AND PHARMACEUTICAL COMPOSITIONS CONTAINING SAME

This invention relates to a novel class of pharmacologically active compounds which exhibit anti-inflammatory, analgesic, immunomodulating and/or anti-pyretic activity.

This invention also relates to pharmaceutical compositions in which the instant products are combined with excipients to provide formulations useful in the treatment of inflammation, pain and/or fever.

Structurally, the compounds of this invention are oxygen and nitrogen containing heterocycles in which the heterocyclic nucleus is substituted by a benzylidene moiety which is also substituted by trifluoromethyl, trimethylsilyl and/or tertiary-alkyl radicals.

BACKGROUND OF THE INVENTION

Many attempts have been made to find a correlation between structure and activity in the treatment of anti-inflammatory diseases but no connection has been found and today researchers will agree only that arthritis is an incurable disease which defies any structure-activity relationships.

This was not always so. In 1980, I. L. Bonta[1] published a review entitled "Progress in Medicinal Chemistry" where he argued convincingly that an association exists between compounds having oxygen-containing radicals as, for example, the phenothiazines, steroids, sulphydryl compounds and copper complexes, and anti-inflammatory activity. This study led to the screening of many compounds as researchers sought to find some interdependence between known anti-oxidants and the effects which those agents produce.

This anti-oxidant theory gained credence in 1985 when K. F. Swingle[2] in an article entitled "Anti-Inflammatory Activity of Antioxidants" offered a rationale for using anti-oxidants to arrest and reverse the degenerative effects of arthritis in mammalian hosts. Swingle urged that since arachidonic acid, an unsaturated acid occuring naturally in fat, is known to undergo enzymatic oxidation in animals and produces pro-inflammatory prostaglandins, any compound which retards or prevents oxidation ought to be a candidate for treating arthritis and the debilitating effects of that disease.

This theory remained in vogue until about 1986 when I. Katsumi reported in the "Chemical and Pharmaceutical Bulletin"[3] that an in-vivo study of several di-(tert-butyl)phenols failed to support the anti-oxidant view. Support for this opinion also appears in a patent to G. Moore (U.S. Pat. No. 4,337,345) where it is stated in Column 1, lines 36–52, that the anti-oxidant activity of 3,5-di(tert-butyl)-4-hydroxytoluene, an additive used to extend the shef-life of food, has little or no value as an anti-inflammatory agent. Moreover, the patentee notes that the absence of anti-inflammatory activity extends also to many other compounds which share the di-(tert-butyl)phenol structure as for example: 2,6-di-(tert-butyl)phenol, 4-carboxamido-2,6-di-(tert-butyl)phenol, 4-(2-chlorobenzoyl)-2,6-di-(tert-butyl)phenol, 4-(5-carboxy-2-chlorobenzoyl)-2,6-di-(tert-butyl)phenol, 2,6-di-(tert-butyl)-4-(phenylsulfonyl)phenol, 4-acetyl-2,6-(di-tert-butyl)phenol and 4-n-octyl-2,6-di-(tert-butyl)-phenol. As a result, G. Moore concluded that there is no correlation which can be drawn between compounds containing the di-(tert-butyl)phenol structure and inflammation and that the effectiveness of compounds in this field can only be ascertained by trial and error (Column 1, lines 63 ∝ 66).

References

1. I. L. Bonta et al; "Progress in Medicinal Chemistry", Vol. 17: page 228; Elsevier/North Holland, Amsterdam (1980).
2. K. F. Swingle et al; "Anti-Inflammatory and Anti-Rheumatic Drugs", Vol. III: Chapter 4 Entitled "Anti-Inflammatory Activity of Antioxidants"; CRC Press, Inc., K. D. Rainsford, Editor (1935).
3. I. Katsumi et al; "Chemical and Pharmaceutical Bulletin", Vol. 34 [4]: pages 1619–1627 (1986).

SUMMARY OF THE INVENTION

The present invention is an advance in the art because it provides a new class of pharmacologically active compounds which are useful in treating arthritis and the degenerative conditions generally associated with that disease.

A further object provides for identifying compounds which have utility as analgesic agents, immunomodulating agents, anti-inflammatory and anti-pyretic agents.

A still further object provides for pharmaceutical compositions in which the aforementioned compounds are combined with excipients to afford formulations which are useful in treating diseases characterized by inflamation, pain and/or fewer.

Still another object is to provide a method for treating diseases characterized by inflammation, pain and/or fever by administering to an affected host a safe and effective amount of a compound of the present invention or a composition containing same.

The compounds of this invention are oxygen and nitrogen containing heterocycles in which the 4-carbon of the heterocyclic nucleus is substituted by benzylidene and the carbons of the benzene ring are substituted by oxy, trifluoromethyl, trimethylsily and/or tertiary-alkyl radicals. These compounds are five, six and seven membered heterocycles which belong to the 3-isoxazolidinone, 2H-1, 2-oxazin-3(4H)-one and 3-isoxazepinone series of compounds and they may be substituted at positions 5, 6 and 7 of the heterocyclic nucleus by various hydrocarbyl moieties.

DETAILED DESCRIPTION

The products of this invention are compounds of the following general formula:

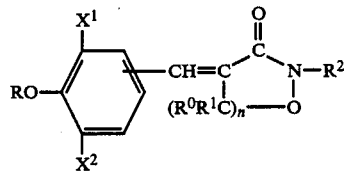

wherein:

R is a member selected from the group consisting of hydrogen, alkyl, alkanoyl, aroyl, alkoxyalkyl, alkoxycarbonyl, lower alkylaminocarbonyl and di-lower alkylaminocarbonyl:

$R^0$, $R^1$ and $R^2$ are the same or different and represent a member selected from the group consisting of hydrogen, lower alkyl, lower alkenyl and lower cycloalkyl;

$X^1$ and $X^2$ are the same or different and represent a member selected from the group consisting of tertiaryalkyl, trimethylsilyl and trifluoromethyl; and n is an integer having a value of 1-3; and the nontoxic pharmacologically acceptable salts thereof.

The compounds of Formula I, supra, may in certain cases be isolated in two isomeric forms identified hereinafter as Isomer-E and Isomer-Z. These isomers correspond to known isomeric forms but their precise structures are new and as such they are considered to be novel compounds falling within the scope of this invention.

Set forth below are definitions of the R, $R^0$, $R^1$ and $R^2$ radicals covered by Formula I.

The term "alkyl" refers to a straight or branched chain alkyl of from about 1-10 carbon atoms. Typical of the alkyl radicals intended are, for example, methyl, ethyl, n-pentyl, isopentyl, hexyl, isohexyl, heptyl, octyl, nonyl and decyl.

The term "alkanoyl" includes, for example, lower alkanoyl of from about 2-6 carbon atoms such as acetyl, propionyl, butyryl, pentanoyl and hexanoyl or the like.

The terms "alkoxyalkyl" and "alkoxycarbonyl" include lower alkoxyalkyl moieties of from about 2-5 carbon atoms as, for example, methoxymethyl, ethoxymethyl, propoxymethyl, 2-methoxyethyl, 5-ethoxypentyl, ethoxycarbonyl and propoxycarbonyl.

The terms "loweralkylaminocarbonyl" and "di-lower alkylaimnocarbony" include, for example, methylaminocarbonyl, dimethylaminocarbonyl and diethylaminocarbonyl or the like.

The term "aroyl" includes mononuclear and binuclear aromatic carbonyl as, for example, benzoyl and naphthoyl or the like.

Typical of the "lower alkenyl" radicals intended are those of from about 2-5 carbon atoms such as vinyl, allyl, isoprenyl, 2-butenyl, 3-methyl-2-butentyl and 3-pentenyl or the like.

Typical of the "lower cycloalkyl" radicals intended are, for example, mononuclear cycloalkyl moieties of from about 3-6 carbon atoms such as cyclopropyl, cyclobutyl, cyclopentyl and cyclohexyl or the like.

Included within this invention are the non-toxic, pharmacologically acceptable salts of the instant products (I). Suitable salts include the acid addition salts and metal salts as, for example, the hydrohalide salts derived from mineral acids such as hydrochloric acid or hydrobromic acid, sulfuric acid, nitric acid or phosphoric acid and the like and organic acid salts derived from such acids as acetic acid, propionic acid, glycolic acid, lactic acid, pyruvic acid, oxalic acid, malonic acid, succinic acid, maleic acid, humeric acid, tartaric acid, citric acid, benzoic acid, cinnamic acid, salicylic acid, 2-phenoxybenzoic acid, 2-acetoxybenzoic acid, mandelic acid, methanesulfonic acid, ethanesulfonic acid, hydroxyethanesulfonic acid, benzenesulfonic acid or toluenesulfonic acid and the like. Suitable metal salts include, for example, the alkali metal or alkaline earth metal salts such as are derived from sodium hydroxide, sodium carbonate, sodium bicarbonate, potassium carbonate, potassium hydroxide or calcium carbonate and the like. Also included are the non-toxic quaternary salts such as are derived from pharmacologically acceptable alkyl halides such as methiodide and ethiodide.

A preferred embodiment of this invention resides in those products wherein the heterocyclic nucleus is a 5-membered ring, that is, a 3-isoxazolidinone, and the benzylidene moiety is substituted by an oxy radical:

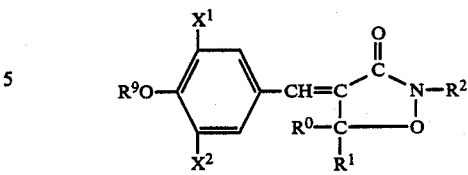

wherein: $R^0$, $R^1$ $R^2$ are the same or different and represent a member selected from the group consisting of hydrogen, lower alkyl, lower alkenyl and lower cycloalkyl;

$R^9$ is a member selected from the group consisting of hydrogen, lower alkanoyl and mononuclear or binuclear aroyl;

$X^1$ and $X^2$ are the same or different and represent a member selected from the group consisting of tert-lower alkyl and trimethylsilyl; and the non-toxic pharmacologically acceptable salts thereof.

The foregoing compounds (II) are uniquely suited for treating the inflammatory effects of rheumatoid arthritis and osteoarthritis and as such they constitute a particularly preferred subgroup of compounds within this invention.

Another preferred embodiment of this invention consists of those products wherein the heterocyclic nucleus is a six membered ring, that is, a 2H-1,2-oxazin-3(4H)-one, and the benzylidene moiety is substituted by an oxy radical:

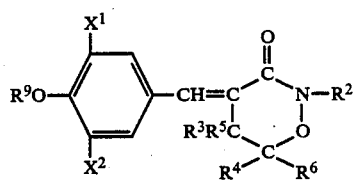

wherein:

$R^2$–$R^6$ are the same or different and represent a member selected from the group consisting of hydrogen, lower alkyl, lower alkenyl and lower cycloalkyl;

$R^9$ is a member selected from the group consisting of hydrogen, lower alkanoyl and mononuclear or binuclear aroyl;

$X^1$ and $X^2$ are the same or different and represent a member selected from the group consisting of terti-arylower alkyl and trimethylsilyl: and the non-toxic pharmacologically acceptable salts thereof.

The above-identified compounds V are also uniquely suited for treating the inflammatory effects of rheumatoid arthritis and osteoarthritis and, in addition, they possess an immunomodulatory effect which makes them particularly effective in the treatment of those diseases.

Still another preferred embodiment of this invention comprises those products in which the heterocyclic nucleus is a seven membered ring, that is, a 3-isoxazepinone, and the benzylidene moiety is substituted by an oxy radical:

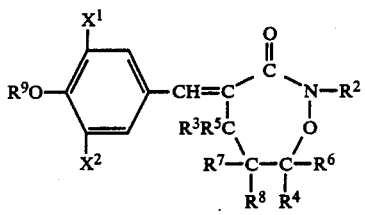

wherein:

$R^2$–$R^8$ are the same or different and represent a member selected from the group consisting of hydrogen, lower alkyl, lower alkenyl and lower cycloalkyl;

$R^9$ is a member selected from the group consisting of hydrogen, lower alkanoyl and mononuclear or binuclear aroyl;

$X^1$ and $X^2$ are the same or different and represent a member selected from the group consisting of terti-ary-lower alkyl and trimethylsilyl: and the non-toxic pharmacologically acceptable salts thereof.

The above-identified compounds VII are also suitable for treating the inflammatory effect of rheumatoid arthritis and osteoarthritis.

SYNTHESIS

The products of this invention are obtained by condensing a benzaldehyde with a heterocyclic α-halo carbonyl (VI) in the presence of zinc according to the Reformatsky Reaction, followed by dehydration of the hydroxymethylene intermediate (III).

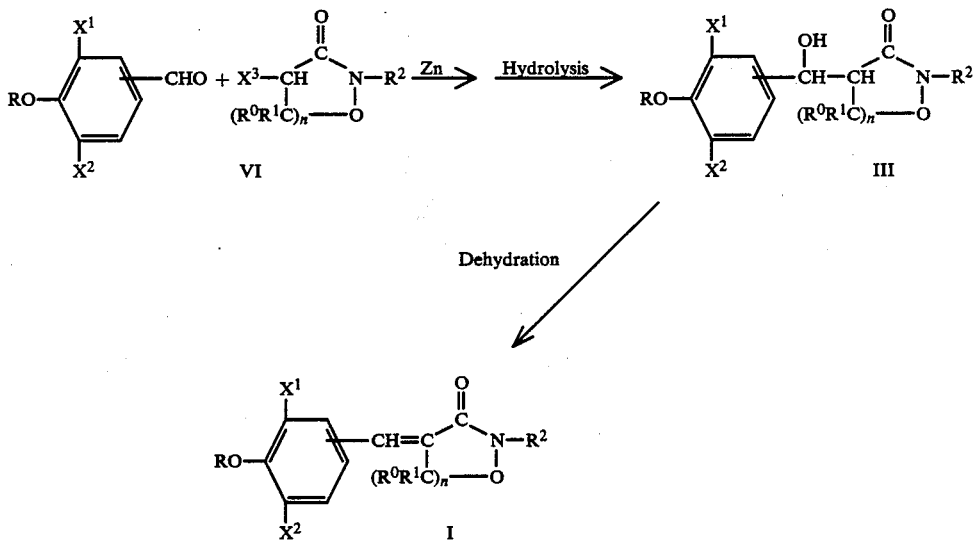

wherein $X^3$ is halo such as chloro, bromo, fluoro or iodo and R, $R^0$, $R^1$, $X^1$, $X^2$ and n are as defined above. The condensation step can be enhanced by conducting the process under reflux in a suitably inert solvent such as benzene and the hydrolysis is conducted under acidic conditions preferably in the presence of a mineral acid such as hydrochloric acid or the like.

Dehydration is achieved by refluxing the hydroxymethyl intermediate (III) under acidic conditions so as to convert the hydroxy radical to a carbonium ion and facilitate the removal of water. Suitable acidic reagents which can be employed in this step include, for example, phosphorous pentoxide and p-toleune sulfonic acid monohydrate.

An alternate method for preparing the instant products (I) consists of treating the hydroxymethylene intermediate (III) with a halogenating agent and subjecting the halomethyl aderivative (IV) thus obtained to dehydrohalogenation. In this procedure the hydroxy radical is first converted to a leaving group, namely, a halo moiety, and the resulting intermediate (IV) is treated with a base to eliminate hydrogen halide. Suitable bases include, for example, hot alcoholic KOH, ammonia, amines or, in certain instances, the bicyclic amidines such as 1,8-diazabicyclo[5.4.0]undec-7-ene:

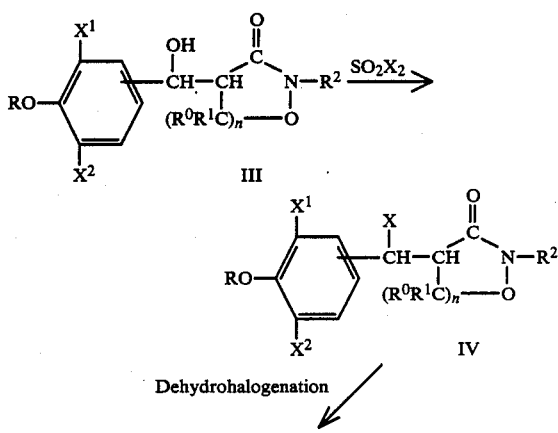

Dehydrohalogenation

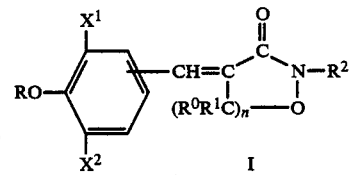

wherein R, $R^0$, $R^1$, $R^2$, $X^1$ and $X^2$ are as defined above and X represents halo such as chloro, bromo, fluoro or iodo and $SO_2X_2$ represents a thionyl halide such as thionyl chloride or thionyl bromide.

In the preceding equation the halogenating agent is thionyl halide but this is for illustration only and it will be appreciated by those skilled in the art that other functionally equivalent reagents such as $PCl_3$, $PCl_5$, $POCl_3$ and hydrogen halides such as hydrogen bromide and hydrogen iodide may be substituted therefor.

The halo substituted starting materials in this process, that is, the heterocyclic α-halo carbonylidentified as VI, supra, are prepared by treating a hydroxylamine with a di-haloalkanoyl halide. This process is conducted in the presence of a base as shown below for the preparation of the 4-halo-3-isoxazolidinone series of compounds:

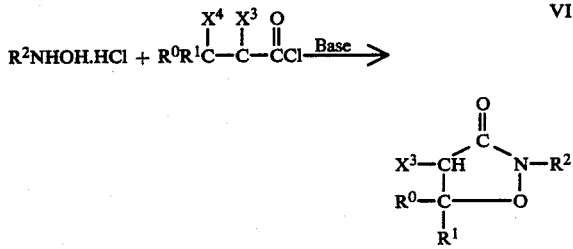

wherein $X^3$ and $X^4$ are halo such as chloro, bromo, iodo or fluoro and $R^0$, $R^1$ and $R^2$ are as defined above. Suitable bases for use in this process include, for example, alkali metal hydroxide and alkali metal carbonate as, for example, sodium hydroxide and potassium carbonate, respectively.

The dihydro-2H-1,2-oxazin-3(4H)-one and tetrahydro-3-isoxazepinone starting materials are obtained in a manner similar to that described in the preceding equation except the propionyl chloride is replaced by a butyryl halide (Equation 1) and a pentanoyl halide (Equation 2) respectively.

$R^2NHOH.HCl\ +$  [1]

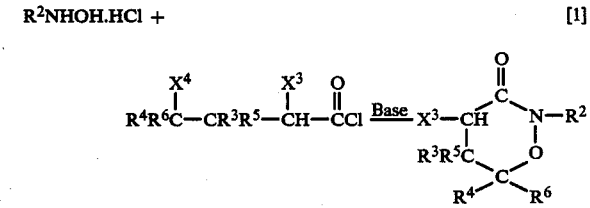

$R^2NHOH.HCl\ +$  [2]

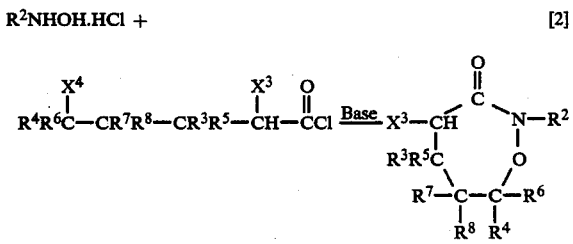

wherein $R^2-R^8$ are as defined above.

PHARMACOLOGY

The compounds (I) of this invention and their non-toxic salts have demonstrated effectiveness in treating inflammation, pain and/or fever in various test systems. Moreover, they exhibit a high level of activity over prolonged periods with little or no evidence of toxicity. Compounds which are particularly useful in treating inflammation and inflammatory diseases such as rheuatoid arthritis and osteoarthritis are those of the following subgroup:

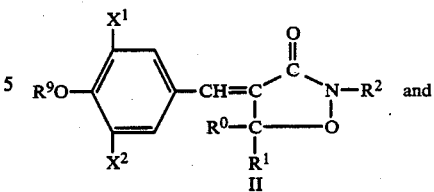

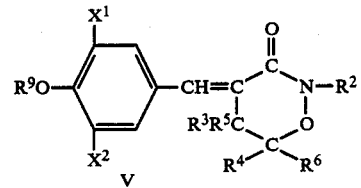

wherein:

$R^0$, $R^1$, $R^2$–$R^9$, $X^1$ and $X^2$ are as defined above; and the non-toxic pharacologically acceptable salts thereof.

The compounds identified as II and V, supra, exhibit surprisingly good anti-inflammatory activity and very favorable therapeutic indexes even at low dosage levels and they maintain their effectiveness over prolonged periods.

Assay: The pharmacologial properties of the present compounds (I) were determined by assay procedures which measured their ability to evoke a characteristic response in test animals.

Anti-Inflammatory: This activity was evaluated via a modification of the Adjuvant Arthritis Assay (AA) described by S. Wong et al in "The Journal of Pharmacology and Experimental Therapeutics", Vol. 185. No. 1: pages 127–138 (1973). This assay measures the ability of the test compound to antogonize local edema, a characteristic of the inflammatory response.

Analgesic: The "Acetylcholine Writhing Assay" (ACH) of collier et al [Nature: Vol. 204: page 1316 (1964)] was employed. In this study the test compounds were administered orally to mice and 45 minutes later the mice were injected with acetylcholine. The frequency of writhing was counted in each animal and the response elicited in the drug-treated mice was compared with the response of those given acetylcholine alone.

Immunomodulatory: This activity was determined by using a Modified Adjuvant Assay procedure in which female rats were injected with *Mycobacterium butyricum* to induce hind paw edema. The test compounds were administered orally and the difference in volume between dosed and non-dosed paws was determined.

Antipyretic: This activity was evaluated by creating a yeast-induced fever in rats according to a modified method of the procedure described by Loux e al in "Toxicology and Applied Pharmacology", Vol. 22: page 672 (1972). In this assay rats injected with yeast in distilled water were dosed with test compounds, aspirin (positive control) and a vehicle (negative control) and the observed differences in body temperature were analyzed statistically.

Antiarthritic: Chronic anti-inflammatory and antiarthritic activities were determined according to the method described by S. Wong in "Tolmetin: A New Non-Steroidal Anti-inflammatory Agent", Editor: John R. Ward, Excerpta Medica, N.J., pages 1–27 (1976). In this assay the differences between dosed and non-dosed paw values were determined postadjuvant.

Formulation: The products (I) of this invention may be employed as the active ingredient in a variety of pharmaceutical compositions in admixture with a pharmaceutically acceptable solid or liquid diluent or carrier. Pharmaceutically acceptable diluents or carriers include any non-toxic substance which, when mixed with a product of this invention renders it more suitable for administration either orally, intravenously or intermuscularly. Typical of the diluents or carriers intended are solid, liquid and semi-solid diluents and carriers such as paraffins, vegetable oils, mannitol, sucrose, glucose or sterile liquids such as water, saline, glycols and oils of a petroleum, animal, vegetable or synthetic origin as, for example, peanut oil, mineral oil and sesame oil. Moreover, the composition may be enhanced by including other useful ingredients such as stabilizers, binders, antioxidants, preservatives, lubricators, suspending agents, viscosity aids or flavoring agents and the like.

The compositions may also include one or more other ingredients having pharmacological activities of their own so as to provide a broad spectrum of activity. For example, in the treatment of inflammation one common complication is the occurrence of edema a condition which may be alleviated by combining a compound of this invention with an appropriate diuretic and/or anoretic. The nature and quantity of these added ingredients will depend largely upon the malady to be treated and the weight of the patient and, therefore, the precise nature of the composition must be left to the practitioner to determine.

Dosage: The dose to be administered depends to a large extent upon the condition being treated and the weight of the host; however, a general daily dosage may consist of from about 0.1 mg to 500 mg. of active ingredient per kilogram of body weight which may be administered in a single dose or multiple doses. A total preferred daily dose lies in the range of from about 0.25 mg. to 100 mg of active ingredient per kilogram of body weight.

Unit Dosage Forms: The compositions of this invention may be administered parenterally or orally in solid and liquid oral unit dosage form as, for example, in the form of tablets, capsules, powders, suspensions, solutions, syrups, sustained release preparations and fluid injectable forms such as sterile solutions and suspensions. The term "unit dosage form" as used in this specification refers to physically discrete units which are administered in single or multiple dosages, each unit containing a predetermined quantity of active ingredient in combination with the required diluent, carrier or vehicle.

Solid Tablets: Hard tablets are prepared by combining the active ingredient, suitably comminuted, with a diluent such as starch, sucrose, kaolin or calcium phosphate and a lubricant. Optionally, the compositions may contain stabilizers, anti-oxidants, preservatives, suspending agents, viscosity aids, flavoring agents and the like. The composition is pressed into tablets and a protective coating of shellac, wax, sugar or polymeric material is added. If desired, dyes can also be included to provide a color-code means for distinguishing between different dosages.

Chewable Tablets: This unit dosage form is prepared by combining the active ingredient with a pharmaceutically acceptable orally ingestible solid carrier and a gum base. If desired, the composition may also contain flavors, binders, lubricants and other excipients.

Soft Capsule: Soft gelatin capsules are prepared by dissolving the active ingredient in a pharmaceutically acceptable oil such as peanut oil, sesame oil or corn oil together with glycerine and water.

Hard Capsule: Hard gelatin capsules may be prepared by mixing the active ingredient with lactose and magnesium stearate and placing the mixture in a No. 3 gelatin capsule. If desired, a glidant such as colloidal silica may also be added to improve flow properties and a distintegrating or solubilizing agent may be included to improve the availability of the medicament upon injection.

Liquids: Syrups, elixirs and suspensions can be prepared in unit dosage form so that the compositions can be administered by the teaspoonful. Syrups are prepared by dissolving the compounds in a suitably flavored aqueous sucrose solution, whereas, elixirs are prepared by combining the active ingredient with non-toxic alcoholic vehicles. Suspensions are obtained by mixing a dry powder containing the active ingredient in water with a minor amount of a suspending agent, a flavoring agent, a sweetener such as sugar and a preservative if necessary.

Parenteral: Unit dosage forms suitable for parenteral administration are prepared by suspending or dissolving a measured amount of the active ingredient in a non-toxic liquid vehicle suitable for injection such as an aqueous or oleaginous medium and sterilizing the resulting mixture.

Alternatively, a measured amount of the active ingredient may be placed in a vial as a discrete entity and the vial and its contents can be sterilized and sealed. If desired, an accompanying vial containing an appropriate vehicle for admixture with said active ingredient can also be provided so that the contents of both vials can be combined and mixed for administration purposes immediately prior to use.

Topical: Powders and other solid unit dosage forms can be formulated by combining an active ingredient of this invention with a suitable carrier such as talc, bentonite, silicic acid, polyamide powder, animal and vegetable fats, wax, paraffins, starch, tragacanth, cellulose derivatives, polyethylene glycols, silicones and zinc oxide or mixtures thereof.

Liquid and semi-liquid formulations, on the other hand can be prepared in the form of suspensions, solutions, ointments, pastes, creams and gels by combining an active ingredient with such carriers as polyethylene glycol, vegetable and mineral oils, alcohols such as isopropanols and the like.

In addition to the aforementioned carriers the formulations can also include such other excipients as emulsifiers, preservatives, colorants, perfumes and the like.

The pH of the formulation should approximate values suitable for application to normal skin, that is, the formulation should possess a pH range of from about 6–6.5 and buffers may be added to the composition to achieve and maintain this pH range. Typical of a buffer which may be used for this purpose is, for example, an aqueous mixture of acetic acid and sodium lactate. The water employed in preparing this buffer should be distilled or demineralised to ensure dermatological acceptability.

EXAMPLE 1

4-(3,5-Di-tert-Butyl-4-Hydroxybenzylidene)-2-Methyl-3-Isoxazolidinone; E and Z Isomers

Step A: 4-Bromo-2-Methyl-3-Isoxazolidinone 2,3-Di-bromopropionyl chloride (25 g, 100 mmol) was added to a stirred mixture of 16.7 g (200 mmol) of N-methyl hydroxylamine hydrochloride and 167 ml of 1N NaOH solution cooled to 0° C. and the reaction mixture was allowed to warm to 25° C. After 2 hours, 200 ml of methylene chloride was added, the mixture was stirred for an additional 8 hours, and the aqueous layer was separated, dried over anhydrous magnesium sulfate and concentrated to yield 23 g of oil. The oil was taken up in 50 ml of methanol, cooled to 0° C. and a 1N NaOH solution (70 ml) was slowly added.

The reaction mixture was allowed to warm to 25° C., stirred for an additional two hours and extracted twice with 100 ml of methylene chloride. The combined organic extracts were dried over anhydrous magnesium sulfate and concentrated to yield 13 g of oil. This oil was chromatographed on silica gel with ethyl acetate to yield 9 g (50 mmol) of 4-bromo-2-methyl-3-isoxazolidinone.

$^1$HNMR (CDCl$_3$) δ 3.23(s,3H), 4.38–4.72 (m,3H):
$^{13}$CNMR (CDCl$_3$)δ 32.38, 42.90, 74.44, 164.04.

Analysis for C$_4$H$_6$Br NO$_2$: Calculated: C,26.69; H,3.36; H,7.78. Found : C,26.74; H,3.66; N,7.70.

Step B: 4-[3,5-Di-tert-Butyl-4-Hydroxyphenyl)Hydroxymethyl]-2-Methyl-3-Isoxazolidinone A mixture of 6 g (33.3 mmol) of 4-bromo-2-methyl-3-isoxazolidinone, 7 g (30 mmol) of 3,5-di-tert-butyl-4-hydroxybenzaldehyde and 3.25 g (50 mmol) of zinc dust in 125 ml of benzene was refluxed with stirring. One hour later another 3 g of zinc dust was added and, after refluxing for an additional 17 hours, the reaction mixture was stirred for five minutes with 200 ml of methylene chloride and 150 ml of 0.5N hydrochloric acid. The organic layer was separated, dried over anhydrous magnesium sulfate and concentrated to yield 10 g of crude material. This material was chromatographed on silica gel with 80% ethyl acetatehexane and recrystallized from ether-hexane to afford 5.7 g (17.1 mmol, 57%) of 4-[(3,5-di-tert-butyl-4-hydroxyphenyl)hydroxymethyl]-2-methyl-3-isoxazolidinone, mp 137°–140° C.

Step C: 4-(3,5-Di-tert-Butyl-4-Hydroxybenzylidene)-2-Methyl-3-Isoxazolidinone; E and Z-Isomers A mixture of 20 g (60 mmol) of 4-[(3,5-di-tert-butyl-4-hydroxyphenyl)hydroxymethyl]-2-methyl-3-isoxazolidinone and 0.4 g of p-toluenesulfonic acid monohydrate in 300 ml of benzene was refluxed for 5 hours. The reaction mixture was concentrated and the concentrate triturated in 150 ml of ether to yield 10 g of the E-isomer of 4-(3,5-di-tert-butyl-4-hydroxybenzylidene)-2-methyl-3-isoxazolidinone having a melting point of 194°–196° C.

The filtrate was concentrated and chromatographed on silica gel (40% ethyl acetate-hexane) to yield 5.4 g of the Z-isomer of 4-(3,5-di-tert-butyl-4-hydroxybenzylidene)-2-methyl-3-isoxazolidinone.

The Z-isomer was recrystallized from pentane to yield 4.7 g of product in the form of white crystals having a melting point of 119.5°–121.5° C.

$^1$HNMR(CDCl$_3$)δ 1.46(s,18H), 3.23(s,3H), 4.97(d,2H) 5.49(s,1H), 6.61(s,1H), 7.99(s,2H);
$^{13}$CNMR(CDCl$_3$)δ, 30.54, 32.81, 34.68, 72.65, 124.94, 126.05, 129.42 134.52, 136.08, 155.88, 164.73:
IR(KBr)cm$^{-1}$ 3255(m), 2950(ms), 1663(ms) 1640(ms) 1481(w), 1433(m), 1395(m), 1213(ms), 1180(w), 1081(mw), 914(mw).

Analysis for C$_{19}$H$_{27}$NO$_3$: Calculated: C,71.89; H,8.50; N,4.41. Found : C,72.16; H,8.56; N,4.10.

The E-isomer obtained according to Step B was combined with an additional 0.9 g of E-isomer obtained from chromatography and the mixture was recrystallized from methylene chloride-ether to yield 9.5 g of the E-isomer of 4-(3,5-di-tert-butyl-4-hydroxybenzylidene)-2-methyl-3-isoxazolidinone in the form of needles having a melting point of 193°–195.5° C.

$^1$HNMR(CDCl$_3$)δ 1.46(s,18H), 3.31(s,3H), 5.23(d,2H), 5.53(s,1H),7.12(s,2H), 7.27(m,1H);
$^{13}$CNMR(CDCL$_3$)δ30.32, 32.40, 34.58, 69.79, 125.04, 126.55, 127.48., 131.50., 137.12, 155.72., 165.06;
IR(KBr)cm$^{-1}$ 3485(m), 2950(m), 1670(ms), 1591(w), 1476(w), 1434(ms), 1395(m), 1356(m), 1277(mw), 1237(mw), 1198(w), 1175(mw), 1147(mw), 1084(ms), 917(mw).

Analysis Calculated for C$_{19}$H$_{27}$NO$_3$: Calculated: C,71.89; H,8.50; N,4.41 Found : C,71.86: H,8.52: N.4.36.

EXAMPLE 2

Dihydro-4-(3,5-Di-tert-Butyl-4-Hydroxybenzylidene)-2-Methyl-2H-1,2-Oxazin-3(4H)-one

Step A: Dihydro-4-Bromo-2-Methyl-2H-1,2-Oxazin-3(4H)-one

To a stirred mixture of 50% sodium hydroxide (8 g) in 25 ml of water and 200 ml of methylene chloride was added 8.4 g (100 mmol) of N-methylhydroxylamine hydrochloride and the resulting mixture was cooled to 5° C. There was slowly added to this mixture 2,4-dibromobutyrylchloride (26.5 g, 100 mmol) followed by the addition of 8.0 g of 50% sodium hydroxide solution in 25 ml of water. Two and a half hours later an additional 8 g of 50% sodium hydroxide solution in 25 ml of water was added and the reaction mixture was allowed to warm to 25° C. After 12 hours, the organic phase was separated, the aqueous layer was extracted with 100 ml of methylene chloride and the organic extracts were combined, dried over anhydrous magnesium sulfate and concentrated to yield 20.1 g of oil. This oil was chromatographed on silica gel with ethyl acetate to yield 10.1 g (52 mmol, 52%) of dihydro-4-bromo-2-methyl-2H-1,2-oxazin-3(4H)-one.

Step B: Dihydro-4-[(3,5-Di-tert-Butyl-4-Hydroxyphenyl)hydroxymethyl]-2-Methyl-2H-12-Oxazin-3(4H)-one A mixture of 8.8 g (45 mmol) of dihydro-4-bromo-2-methyl-2H-1,2-oxazin-3(4H)-one, 9.4 g (40 mmol) of 3,5-di-tert-butyl- 4-hydroxybenzaldehyde and 5.9 g of zinc dust (90 mmol) in 150 ml of benzene was refluxed with stirring for 17 hours. The mixture was treated with 250 ml of 1N hydrochloric acid for a few minutes and filtered. The filtrate was extracted twice with 200 ml portions of methylene chloride and the combined organic extracts were dried over anhydrous magnesium sulfate and concentrated to afford 19.1 g of solid. This solid was chromatographed on silica gel with 40% ethyl acetate-hexane to yield 7 g (20 mmol, 50%) of solid dihydro-4-[(3,5-di-tert-butyl-4-hydroxyphenyl)hydroxymethyl]-2-methyl-2H-1,2-oxazin-3(4H)-one.

Step C:
Dihydro-4-(3,5-Di-tert-Butyl-4-Hydroxybenzylidene)-2-Methyl-2H-1,2-Oxazin-3(4H)-one The dihydro-4-[(3,5-di-tert-butyl-4-hydroxyphenyl)-hydroxymethyl]-2-methyl-2H-1,2-oxazin-3(4H)-one (7.0 g, 20 mmol) obtained according to Step B was added to 100 ml of benzene and 0.4 g of p-toluenesulfonic acid monohydrate and refluxed for 34 hours. The mixture was concentrated to approximately 20 ml, taken up in 250 ml of methylene chloride, washed with dilute sodium bicarbonate solution, dried over anhydrous magnesium sulfate and concentrated to a solid (6.8 g) which was recrystallized from acetone to yield 3 g of product. The mother liquor was concentrated and chromatographed on silica gel with 45% ethyl acetate-hexane to yield 2.5 g of additional product which was combined with the earlier crop and recrystallized from acetone-hexane to afford a total yield of 5.1 g of crystalline dihydro-4-(3,5-di-tert-butyl-4-hydroxybenzylidene)-2-methyl-2H-1,2-oxazin-3(4H)-one, melting point 171°–172° C.

$^1$HNMR (CDCl$_3$)δ 1.47(s,18H), 3.03(m,2H), 3.34(s,3H), 4.20(t,2H), 5.47(s,1H), 7.32(s,2H), 7.76(m,1H): $^{13}$CNMR(CDCl$_3$)δ 29.18, 30.43, 34.61,34.93, 69.68, 122.04, 127.40, 128.08, 136.49, 138.02, 155.14, 165.00.

IR(KBr)cm$^{-1}$ 13200(broad), 2950(m), 1634(mw), 1571(s), 1467(w), 1433(m), 1389(mw), 1194(m), 1161(w).

Analysis for C$_{20}$H$_{29}$NO$_3$: Calculated: C,72.47; H,8.82; N,4.22 Found : C,72.41; H,8.71; N,4.31.

EXAMPLE 3

4-(3,5-Di-tert-Butyl-4-Hydroxybenzylidene)-2-Ethyl-3-Isoxazolidinone

Step A: 4-Bromo-2-Ethyl-3-Isoxazolidinone

To a stirred mixture of 20.85 g (0.3 mol) of hydroxylamine hydrochloride in 250 ml of methanol there was added 16.2 g (0.3 mol) of sodium methoxide and, ten minutes later, 16.8 ml (0.3 mol) of acetaldehyde. To the resulting acetoxime solution was added 13.2 g (0.21 mol) of sodium cyanoborohydride, a trace of methyl orange and a solution of 13% HCl-Methanol with stirring to maintain the red color (pH3). The mixture was stirred for three hours, the methanol was removed under reduced pressure and 24 g (0.3 mol) of 50% sodium hydroxide in 75 ml of water was added to the residue.

The mixture was cooled to 0° C. and 75 g (0.3 mol) of 2,3-dibromopropionyl chloride was added slowly to the stirred mixture followed by 24 g (0.3 mol) of 50% sodium hydroxide solution in 75 ml of water. Thirty minutes later, 300 ml of methylene chloride was added followed by the addition of 24 g (0.3 mol) of 50% sodium hydroxide solution in 75 ml of water. Stirring was continued and the temperature maintained at 0° C. for 2 hours. The organic layer was separated, dried over anhydrous magnesium sulfate, filtered and the filtrate concentrated to afford 35 g of crude product. This product was chromatographed on silica gel with 40% ethyl acetate-hexane to yield 10 g (52 mmol) of 4-bromo-2-ethyl-3-isoxazolidinone in the form of an oil.

$^1$HNMR(CDCl$_3$):δ 1.25(t,3H), 3.66(q,2H), 4.37–4.67(m,3H).

Step B:
4-(3,5-Di-tert-Butyl-4-Hydroxybenzylidene)-2-Ethyl-3-Isoxazolidinone

A mixture of 4.4 g (23 mmol) of 4-bromo-2-ethyl-3-isoxazolidinone, 4.9 g (21 mmol) of 3,5-di-tert-butyl-4-hydroxybenzaldehyde and 4.1 g (60 mmol) of zinc dust in 100 ml of benzene was refluxed for 12 hours. Methylene chloride (124 ml) and 100 ml of 0.5N hydrochloric acid were added and the mixture was slurried for a few minutes and filtered. The organic layer was separated, dried over anhydrous magnesium sulfate and concentrated to yield 9 g of the crude intermediate 4-[(3,5-di-tert-butyl-4-hydroxyphenyl)hydroxymethyl]-2-ethyl-3-isoxazolidinone.

The intermediate and 0.18 g of p-toluenesulfonic acid monohydrate in 130 ml of benzene were refluxed for 2 hours and concentrated to a solid which was recrystallized from ether to yield 0.89 g of 4-(3,5-di-tert-butyl-4-hydroxybenzylidene)-2-ethyl-3-isoxazolidinone, mp 189°–191° C. The mother liquor was chromatographed on silica gel with 40% ethyl acetate-hexane and recrystallized from ether to yield 1.4 g of additional product having a melting point of 188°–189° C.

(CDCl$_3$)δ 1.28(t,3H), 1.47(s,18H), 3.75(q,2H), 4.23(d,2H), 5.52(s,1H), 7.12(s,2H), 7.24(m,1H). $^{13}$CNMR(CDCl$_3$)δ 12.50, 30.32, 34.58, 40.68, 69.78, 125.58, 126.62, 127.44, 131,35, 137.06, 155.67, 164.37.

Analysis for C$_{20}$H$_{29}$NO$_3$: Calculated: C,72.47; H,8.82; N,4.22. Found : C,72.52; H,8.96: N,4.39.

EXAMPLE 4

4-(3,5-Di-tert-Butyl-4-Hydroxybenzylidene)-2-n-Propyl-3-Isoxazolidinone

Step A: 4-Bromo-2-n-Propyl-3-Isoxazolidinone

To a stirred mixture of 6.95 g (100 mmol) of hydroxylamine hydrochloride, 5.4 g (100 mmol) of sodium methoxide and 5.8 g (100 mmol) of propionaldehyde in 110 ml of methanol there was added 4.4 g (70 mmol) of sodium cyanoborohydride, a trace of methyl orange and a solution of 13% HCl-Methanol sufficient to maintain the red color (pH3). The mixture was stirred for two hours, the methanol was removed under reduced pressure and 100 ml of 1N sodium hydroxide was added to the residue.

The mixture was cooled to 0° C. and 25 g (100 mmol) of 2,3-dibromopropionyl chloride was slowly added followed by the addition of 1N sodium hydroxide (100 ml). Ten minutes later, 200 ml of methylene chloride and 100 ml of 1N sodium hydroxide were added and stirring was continued for two hours. The organic phase was separated, dried over anhydrous magnesium sulfate and concentrated to a crude oil (9 g). This oil was chromatographed on silica gel with 60% ethyl acetate-hexane to yield 4 g of 4-bromo-2-n-propyl-3-isoxazolidinone.

$^1$HNMR (CDCL$_3$)δ 0.97(t,3H), 1.71(sextet,2H), 3.58(t,2H), 4.37–4.68(m,3H).

Step B:
4-(3,5-Di-tert-Butyl-4-Hydroxybenzylidene)-2-n-Propyl-3-Isoxazolidinone

A mixture of 4 g (20 mmol) of 4-bromo-2-n-propyl-3isoxazolidinone, 4.2 g (18 mmol) of 3,5-di-tert-butyl-4hydroxybenzaldehyde and 4.1 g (60 mmol) of zinc dust in 100 ml of benzene was refluxed for 18 hours. Methylene chloride (125 ml) and 100 ml of 0.5N hydrochloric acid were added and the resulting mixture was stirred for a few minutes and filtered. The organic layer was then separated, dried over anhydrous magnesium sulfate and concentrated. The concentrate was chromatographed on silica gel with 40% ethyl acetatehexane to yield 4.7 g of the intermediate-4-[(3,5-di-tert-butyl-4-hydroxyphenyl)hydroxymethyl]-2-n-propyl-3-isoxazolidinone.

The intermediate and 0.1 g of p-toluenesulfonic acid monohydrate in 80 ml of benzene were refluxed for three hours and concentrated to a solid which upon recrystallization from ether yielded 2.0 g of 4-(3,5-di-tert-butyl-4-hydroxybenzylidene)-2-n-propyl-3-isoxazolidinone, mp 194°–196° C.

$^1$HNMR(CDCl$_3$)$\delta$ 0.96(t,3H), 1.45(s,18H), 1.72(m,2H), 3.68(t,2H), 5.23(d,2H), 5.52(s,1H), 7.11(s,2H), 7.24(m,1H).

Analysis for C$_{21}$H$_{31}$NO$_3$: Calculated: C,73.01; H,9.04; N,4.05. Found : C,72.98; H,8.87: N,4.01.

EXAMPLE 5

4-(3,5-Di-tert-Butyl-4-Hydroxybenzylidene)-2,5-Dimethyl-3-Isoxazolidinone

Step A: 4-Bromo-2,5-Dimethyl-3-Isoxazolidinone

To a stirred mixture of 12.5 g (150 mmol) of N-methylhydroxylamine hydrochloride, 20.7 g (150 mmol) of potassium carbonate and 4.1 g (15 mmol) of tetrabutylammonium hydrogen sulfate in 250 ml of methylene chloride, there was added 2, 3-dibromobutyryl chloride (42 g,150 mmol) followed by the addition of 41.4 g (300 mmol) of potassium carbonate. After three days the mixture was filtered, the filtrate was concentrated and the concentrate was chromatographed on silica gel with 40% ethyl acetate-hexane to afford 16.8 g (86 mmol, 57%) of 4-bromo-2,5-dimethyl-3-isoxazolidinone.

$^1$HNMR (CDCl$_3$)$\delta$ 1.45 and 1.46 (both d,total 3H) 3.20 and 3.22(both s, total 3H), 4.33–4.58(m,2H).

Step B:
4-(3,5-Di-tert-Butyl-4-Hydroxybenzylidene)-2,5-Dimethyl-3-Isoxazolidinone A mixture of 1.4 g (7.2 mmol) of 4-bromo-2,5-dimethyl-3-isoxazolidinone, 1.54 g (6.6 mmol) of 3,5-di-tert-butyl-4-hydroxybenzaldehyde and 1.43 g (22 mmol) of zinc dust in 75 ml of benzene was refluxed for 18 hours. Methylene chloride (100 ml) and 100 ml of 0.5N hydrochloric acid were added and the mixture was stirred for a few minutes and filtered following which the organic layer was separated, dried over anhydrous magnesium sulfate and concentrated. The concentrate was chromatographed on silica gel with 40% ethyl acetate-hexane to yield 1.2 g of the intermediate 4-[(3,5-di-tert-butyl-4-hydroxyphenyl)hydroxymethyl]-2,5-dimethyl-3-isoxazolidinone.

The intermediate thus obtained and 0.03 g of p-toluenesulfonic acid monohydrate in 50 ml of benzene were refluxed for 3 hours. The concentrate was chromatographed on silica gel with 40% ethyl acetate-hexane to yield, upon trituration with ether-hexane, 0.81 g of the product 4-(3,5-di-tert-butyl-4-hydroxybnzylidene)-2,5-dimethyl-3-isoxazolidinone, mp. 147°–150° C.

$^1$HNMR(CDCl$_3$)$\delta$ 1.46(s,18H), 1.55(d,3H), 3.31(s,3H), 5.53(s,1H), 5.60(m,1H), 7.17–7.29(m,3H).

Analysis for C$_{20}$H$_{29}$NO$_3$: Calculated: C,2.47; H,8.82; N,4.22. Found : C,72.50; H,8.91; N,4.13.

EXAMPLE 6

4-(3,5-Di-tert-Butyl-4-Hydroxybenzylidene)-2-Isopropyl-3-Isoxazolidinone

Step A: 4-Bromo-2-Isopropyl-3-Isoxazolidinone

To a stirred mixture of 6 g (25 mmol) of N-isopropylhydroxylamine oxalate and 1N sodium hydroxide (50 ml) in water (100 ml) cooled to 0° C. there was added 2,3-dibromopropionyl chloride (12.5 g, 50 mmol), followed by the addition of 50 ml of 1N sodium hydroxide. Ten minutes later, 150 ml of methylene chloride and 60 ml of 1N sodium hydroxide were added. The mixture was stirred continuously for one hours following which the organic phase was separated, dried over anhydrous magnesium sulfate and concentrated. The concentrate was chromatographed on silica gel with 40% ethyl acetatehexane to afford 3.3 g of 4-bromo-2-isopropyl-3-isoxazolidinone.

$^1$HNMR(CDCl$_3$)$\delta$ 1.28(d,6H), 4.27–4,68(m,4H).

Step B:
4-(3,5-Di-tert-Butyl-4-Hydroxybenzylidene)-2-Isopropyl-3-Isoxazolidine

A mixture of 3.51 g (15 mmol) of 3,4-di-tert-butyl-4-hydroxybenzaldehyde, 2.8 g (13.4 mmol) of 4-bromo-2-isopropyl-3-isoxazolidinone and 2.5 g of zinc dust in 50 ml of benzene was refluxed for two and a half hours. The mixture was concentrated and chromatographed on silica gel with 50% ethyl acetate-hexane to yield 3.7 g of the intermediate, 4-[(3,5-di-tert-butyl-4-hydroxyphenyl)hydroxymethyl]-2-isopropyl-3-isoxazolidinone. This intermediate was refluxed in 30 ml of benzene with 0.1 g of p-toluenesulfonic acid monohydrate for 3 hours. The mixture was concentrated and recrystallized from ether to yield 2.25 g (6.5 mmol, 40%) of 4-(3,5-di-tert-butyl-4-hydroxybenzylidene)-2-isopropyl-3-isoxazolidinone, mp 178°–180° C.:

$^1$HNMR(CDCl$_3$)$\delta$1.30(d,6H), 1.45(s,18H), 4.55(m,1H), 5.22(d,2H), 5.51(s,1H), 7.11(s,1H), 7.25(m,1H).

Analysis for C$_{21}$H$_{31}$NO$_3$: Calculated: C,73.01; H,9.04; N,4.05. Found : C,73.12: H,8.94; N,4.03.

EXAMPLE 7

Tetrahydro-4-(3,5-Di-tert-Butyl-4-Hydroxybenzylidene)-2-Methyl-3-Isoxazepinone

Step A:
Tetrahydro-4-Bromo-2-Methyl-3-Isoxazepinone

To a stirred mixture of 12.5 g (150 mmol) of N-methylhydroxylamine hydrochloride, 20.7 g (150 mmol) of potassium carbonate and 5.1 g (15 mmol) of tetrabutyl-ammonium hydrogen sulfate in 300 ml of methylene chloride, there was added 2,5-dibromovaleryl chloride (41.7 g, 150 mmol) followed by the addition of 41.4 g (300 mmol) of potassium carbonate. After 3 days the mixture was filtered, the filtrate was concentrated and the concentrate was chromatographed on silica gel with ethyl acetate to afford 15.2 g (73 mmol, 49%) of oily tetrahydro-4-bromo-2-methyl-3-isoxazepinone.

Step B:
Tetrahydro-4-(3,5-Di-tert-Butyl-4-Hydroxybenzylidene)-2-Methyl-3-Isoxazepinone A mixture of 6.2 g (30 mmol) of tetrahydro-4-bromo-2-methyl-3-isoxazepinone, 2.34 g (10 mmol) of 3,5-ditert-butyl-4-hydroxybenzaldehyde and 3.9 g (60 mmol) of zinc dust in 200 ml of benzene was refluxed with stirring for 5 days. Methylene chloride (100 ml) and 100 ml of 0.5N hydrochloric acid were then added and the mixture was slurried for a few minutes and filtered. The resulting organic phase was separated, dried over anhydrous magnesium sulfate and concentrated in vacuo to afford 4.8 g of a crude material which was chromatographed on silica gel with 40% ethyl acetate-hexane to yield 600 mg of an intermediate identified as tetrahydro-4-[(3,5-di-tert-butyl-4-hydroxyphenyl)hydroxymethyl]-2-methyl-3-isoxazepinone. From the chromatography there was also obtained 600 mg of the final product, tetrahydro-4-(3,5-di tert-butyl-4-hydroxybenzylidene)-2-methyl-3-isoxazepinone.

The intermediate was refluxed with 30 mg of p-toluenesulfonic acid monohydrate in 80 ml of benzene for 4 hours. The mixture was then concentrated and the crude tetrahydro4-(3,5-di-tert-butyl-4-hydroxybenzylidene)-2-methyl-3isoxazepinone (500 mg) thus obtained was combined with 600 mg of the product obtained earlier and was chromatographed on silica gel with 50% ethyl acetate-hexane. The product was then triturated in hexane to afford 850 mg of crystalline tetrahydro-4-(3,5-di-tert-butyl-4-hydroxybenzylidene)-2-methyl-3-isoxazepinone having a melting point of 127°–129° C.

$^1$HNMR(CDCl$_2$)δ1.44(s,18H), 1.98(m,2H), 2.72(m,2H), 3.23(s,3H), 4.03(t,2H), 5.33(s,1H), 7.25(s,2H), 7.26(m,1H). $^{13}$CNMR(CDCl$_3$)δ26.36, 26.49, 30.49, 34.39, 34.62, 72.56, 127.50, 127.73, 133.61, 136.28, 137.38, 154.46, 173.52.

Analysis for C$_{21}$H$_{31}$NO$_3$: Calculated: C,73.00; H,9.04: N,4.05. Found : C,72.82: H,8.98; N,3.97.

EXAMPLE 8

Dihydro-4-(3,5-Di-tert-Butyl-4-Hydroxybenzylidene)-2-Isopropyl-2H-1,2-Oxazin-3(4H)-one

Step A:
Dihydro-4-Bromo-2-Isopropyl-2H-1,2-Oxazin-3(4H)-One

To a stirred mixture of 5.3 g (47 mmol) of N-isopropylhydroxylamine hydrochloride in 100 ml of methylene chloride cooled to 5° C. was added 3.8 g (47 mmol) of 50% sodium hydroxide solution in 20 ml of water. To this mixture was added with stirring 12.4 g (47 mmol) of 2,4-dibromobutyrylchloride and twenty minutes later an additional 7.6 g (94 mmol) of 50% sodium hydroxide solution was added. After twenty hours the organic phase was separated, dried over anhydrous magnesium sulfate and concentrated to an oil. This oil was chromatographed on silica gel with 40% ethyl acetate-hexane to afford 1.1 g of oily dihydro-4-bromo-2-isopropyl-2H-1,2-oxazin-3(4H)-one.

Step B:
Dihydro-4-[(3,5-Di-tert-Butyl-4-Hydroxyphenyl)hydroxymethyl]-2-Isopropyl-2H-1,2-Oxazin-3(4H)-One A stirred mixture of 1.1 g (5 mmol) dihydro-4-bromo-2-isopropyl-2H-1,2-oxazin-3(4H)-one, 1.2 g (5 mmol) of 3,5-di-tert-butyl-4-hydroxybenzaldehyde and 1 g of zinc dust in 20 ml of benzene were refluxed for 15 hours and concentrated. The concentrate was taken up in methylene chloride and chromatographed on silica gel with 30% ethyl acetate-hexane to yield 1.2 g of dihydro-4-[(3,5-di-tert-butyl-4-hydroxyphenyl)hydroxymethyl]-2-isopropyl-2H-1,2-oxazin-3(4H)-one, mp 150°–153° C.

Step C:
Dihydro-4-(3,5-Di-tert-Butyl-4-Hydroxybenzylidene)-2-Isopropyl-2H-1,2-Oxazin-3(4H)-One The dihydro-4-[(3,5-di-tert-butyl-4-hydroxyphenyl)-hydroxymethyl]-2-isopropyl-2H-1,2-oxazin-3(4H)-one of Step B was refluxed in 40 ml of benzene with a catalytic amount of p-toluenesulfonic acid monohydrate for 6 hours and concentrated in vacuo. The concentrate was triturated in ether and filtered to yield 0.9 g (2.5 mmol) of dihydro-4-(3,5-di tert-butyl-4-hydroxybenzylidene)-2-isopropyl-2H-1,2-oxazin-3(4H)-one, mp 181°–183° C.

$^1$HNMR(CDCl$_3$)δ1.24(d,6H), 1.45(s,18H), 3.03(m,2H), 4.16(t,2H), 4.92(m,1H), 7.32(s,2H), 7.76(m,1H).

An alternate method for preparing this product is illustrated by the following embodiment.

EXAMPLE 9

4-(3,5-Di-tert-Butyl-4-Hydroxybenzylidene)-2-Methyl-3-Isoxazolidinone, E-Isomer

To a stirred solution of 3.3 g (9.8 mmol) of dihydro-4[(3,5-di-tert-butyl-4-hydroxyphenyl)hydroxymethyl]-2-methyl-3-isoxazolidinone in 50 ml of methylene chloride there was added 0.73 ml (10 mmol) of thionyl chloride. After two hours the reaction mixture was concentrated in vacuo. The resulting intermediate, 4-[(3,5-di-tert-butyl-4-hydroxyphenyl)chloromethyl]-2-methyl-3-isoxazolidinone was dissolved in 150 ml of methylene chloride and 1.5 g (10 mmol) of triethylamine was added with stirring. After ten minutes the mixture was washed with dilute hydrochloric acid, dried over anhydrous magnesium sulfate and concentrated to a solid. The solid was triturated in methylene chloride-ether to yield 2.85 g (9 mmol, 92%) of a crystalline product identified as the E-isomer of 4-(3,5-di-tert-butyl-4-hydroxybenzylidene)-2-methyl-3-isoxazolidinone, mp 193°–196° C.

EXAMPLE 10

Dihydro-4-(3,5-Di-tert-Butyl-4-Hydroxybenzylidene)-2-Ethyl-2H-1,2-Oxazin-3-(4H)-One

Step A:
Dihydro-4-Bromo-2-Ethyl-2H-1,2-Oxazin-3(4H)-One

To a stirred mixture of 10.4 g (0.15 mol) of hydroxylamine hydrochloride in 100 ml of methanol there was added 8.1 g (0.15 mol) of sodium methoxide and, ten minutes later, 6.6 g (0.15 mol) of acetaldehyde. To the resulting acetoxime solution was added 6.3 g (0.1 mol) of sodium cyanoborohydride, a trace of methyl orange and a solution of 13% HCL-Methanol with stirring sufficient to maintain the red color (pH3). The mixture was stirred for two days, the methanol was removed under reduced pressure and there was added 10 g of 50% sodium hydroxide in 100 ml of water, 2.2 g of benzyltriethylammonium chloride and 400 ml of methylene chloride.

The mixture was cooled to 0° C. and 26.5 g (100 mmol) of 2,4-dibromo-butyrylchloride dissolved in 50 ml of methylene chloride was added followed by the addition fifteen minutes later of 8 g (75 mmol) of anhydrous sodium carbonate. Two hours later an additional 11 g (104 mmol) of anhydrous sodium carbonate and 100 ml of water was added, the mixture was stirred continuously for 27 hours and then acidified with 1 N hydrochloric acid. The organic layer was separated and the resulting mixture was concentrated to approximately 50 ml and chromatographed on silica gel with 60% ethyl acetate-hexane to yield 11.8 g (56 mmol, 50%) of dihydro-4-bromo-2-ethyl-2H-1,2-oxazin-3(4H)-one.

Step B:
Dihydro-4-[(3,5-Di-tert-Butyl-4-Hydroxyphenyl) hydroxymethyl]-2-Ethyl-2H-1,2-Oxazin-3(4H)-One A mixture of 11.7 g (56 mmol) of dihydro-4-bromo-2-ethyl-2H-1,2-oxazin-3(4H)-one, 13.2 g (56 mmol) of 3,5-di-tert-butyl-4-hydroxybenzaldehyde and 14 g (214 mmol) of zinc dust in 400 ml of benzene was refluxed with stirring for 22 hours. The mixture was filtered and the solid washed with methylene chloride. The combined filtrates were concentrated to 50 ml and chromatographed on silica gel with 60% ethyl acetate-hexane to yield 15.1 g (41.5 mmol, 74%) of solid dihydro-4-[(3,5-di-tert-butyl-4-hydroxyphenyl)hydroxymethyl]-2-ethyl-2H-1,2-oxazin-3(4H)-one.

Step C:
Dihydro-4-(3,5-Di-tert-Butyl-4-Hydroxybenzylidene)-2-Ethyl-2H-1,2-Oxazin-3(4H)-One The dihydro-4-[(3,5-di-tert-butyl-4-hydroxyphenyl)-hydroxymethyl]-2-ethyl-2H-1,2-oxazin-3(4H)-one (15 g, 41 mmol) obtained according to Step B was added to 100 ml of benzene and 0.4 g of p-toluenesulfonic acid monohydrate and refluxed for 13 hours. The mixture was concentrated to a solid, taken up in 150 ml of methylene chloride, washed with dilute sodium bicarbonate solution, dried over anhydrous magnesium sulfate and concentrated to a brown solid (14.1 g) which was recrystallized from acetone to yield 6.4 g of crystalline dihydro-4-(3,5-di-tert-butyl-4-hydroxybenzylidene)-2-ethyl-2H-1,2-oxazin-3(4H)-one having a melting point of 166°-167° C.

$^1$HNMR(CDCl$_3$)δ1.25(t,3H), 1.45 (s,18H), 3.04(m,2H), 3.81(q,2H), 4.19(t,2H), 5.44(s,1H), 7.31(s,2H), 7.76(m,1H); $^{13}$CNMR(CDCl$_3$)δ12.32, 29.26, 30.44, 34.62, 42.38, 70.17, 122.33, 127.47, 128.04, 136.48, 138.01, 155.10, 164.11.

IR(KBr)cm$^{-1}$3245(broad), 2950(m), 1634(mw), 1566(ms), 1433(m), 1355(w), 1202(mw), 1175(mw).

Analysis for C$_{21}$H$_{31}$NO$_3$; Calculated: C,73.00: H,9.04: N,4.05 Found : C,72.98; H,9.02; N,4.03.

EXAMPLE 11

Dihydro-4-(3,5-Di-tert-Butyl-4-Methoxybenzylidene)-2-Methyl-2H-1,2-Oxazin-3(4H)-One Sodium hydride (0.33 g, 8.3 mmol), 60% in mineral oil dispersion, kept under nitrogen purge, was washed twice with 20 ml portions of hexane. Dimethyl sulfoxide (10 ml) was added, followed by the addition of 2.5 g (7.6 mmol) of dihydro-4-(3,5-di-tert-butyl-4-hydroxybenzylidene)-2-methyl-2H-1,2-oxazin-3(4H)-one. Gas evolution was observed and the mixture became yellow following which an additional 5 ml of dimethyl sulfoxide was added. One hour later, 1.1 g (7.7 mmol) of methyl iodide was added and the mixture was stirred for 50 hours. The reaction mixture was diluted with 75 ml of water and precipitation occurred in the form of crystals which were collected and air dried to yield 3.3 g of crude product. Recrystallization from acetone-hexane afforded 1.85 g (5.4 mmol, 71%) of dihydro-4-(3,5-di-tert-butyl-4-methoxybenzylidene)-2-methyl-2H-1,2-oxazin-3(4H)-one having a melting point of 119°-121° C.

$^1$HNMR(CDCl$_3$)δ1.45(s,18H), 3.04(m,2H), 3.35(s,3H), 3.70(s,3H), 4.20(t,2H), 7.34(s,2H), 7.76(m,1H).

Analysis for C$_{21}$H$_{31}$NO$_3$: Calculated: C,73.00; H,9.04; N,4.05. Found : C,72,76: H,8.98: N,4.03.

All products covered by this invention may be obtained by following the procedure described in the preceding embodiments. The following equation illustrates the procedure of Example 1, Steps A, B and C and, together with Table I, infra, illustrates the hydroxylamine, alkanoyl halide and aldehyde starting materials employed in this process and the isoxazolidinone products obtained thereby:

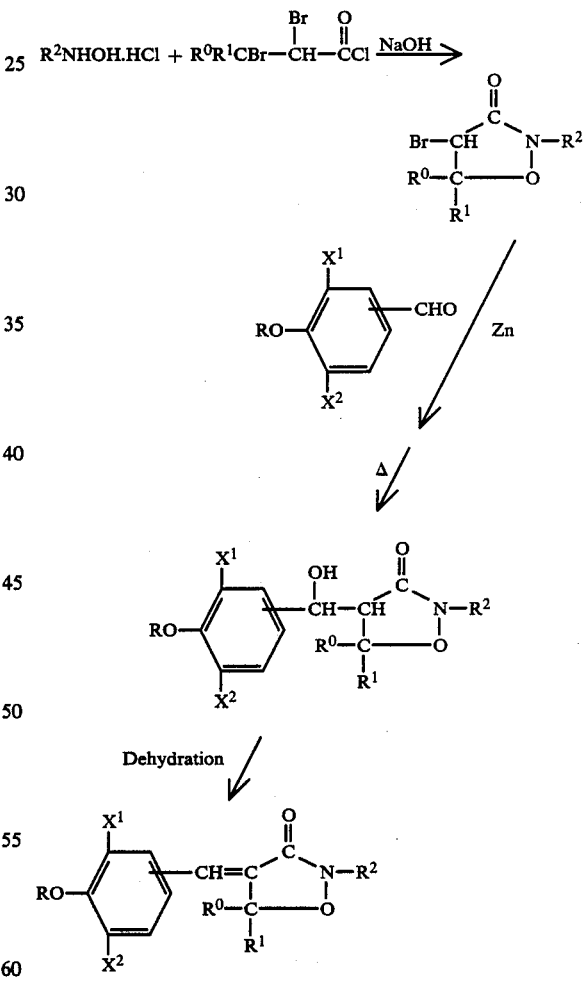

TABLE I

| Ex. | R | R$^0$ | R$^1$ | R$^2$ | X$^1$ | X$^2$ |
|---|---|---|---|---|---|---|
| 12 | —COCH$_3$ | H | H | —CH$_3$ | —C(CH$_3$)$_3$ | —C(CH$_3$)$_3$ |
| 13 | —COOCH$_3$ | H | H | —CH$_3$ | —C(CH$_3$)$_3$ | —C(CH$_3$)$_3$ |
| 14 | H | H | H | —CH$_3$ | —Si(CH$_3$)$_3$ | —Si(CH$_3$)$_3$ |
| 15 | H | H | H | —CH$_3$ | —CF$_3$ | —CF$_3$ |

TABLE I-continued

| Ex. | R | R⁰ | R¹ | R² | X¹ | X² |
|---|---|---|---|---|---|---|
| 16 | H | H | —CH₂CH=CH₂ | —CH₃ | —C(CH₃)₃ | —C(CH₃)₃ |
| 17 | H | H | —CH(CH₂CH₂) (cyclopropyl) | —CH₃ | —C(CH₃)₃ | —C(CH₃)₃ |
| 18 | H | H | H | —CH₂CH=CH₂ | —C(CH₃)₃ | —C(CH₃)₃ |
| 19 | H | H | H | —CH(CH₂CH₂) (cyclopropyl) | —C(CH₃)₃ | —C(CH₃)₃ |
| 20 | H | —CH₃ | —CH₃ | —CH₃ | —C(CH₃)₃ | —C(CH₃)₃ |

The dihydro-2H-1,2-oxazin-3-(4H)-ones of this invention are obtained in a manner similar to that described in the preceding equation except that 2,4-dihaloalkanoyl chloride is substituted for 2,3-dibromoalkanoyl halide and the procedure of Example 2 is followed. This procedure is illustrated by the following equation which, in combination with Table II, infra, illustrates the starting materials of this process and the products obtained thereby. When R in the following equation is hydrogen the resulting dihydro 4-(4-hydroxybenzylidene)-2H-1,2-oxazin-3(4H)-one may be converted to a dihydro-4-(4-oxybenzylidene)-2H-1,2-oxazin-3(4H)-one via treatment with a base and a halide of the formula RX wherein R and X are as defined above. Suitable bases which may be used in this step include, for example, the alkali metal hydrides such as sodium hydride. Moreover this step may also be used to convert the 4-(4-hydroxybenzylidene)-3-isoxazolidinone and isoxazepinone series of compounds to their corresponding oxy derivatives.

R²NHOH·HCl +

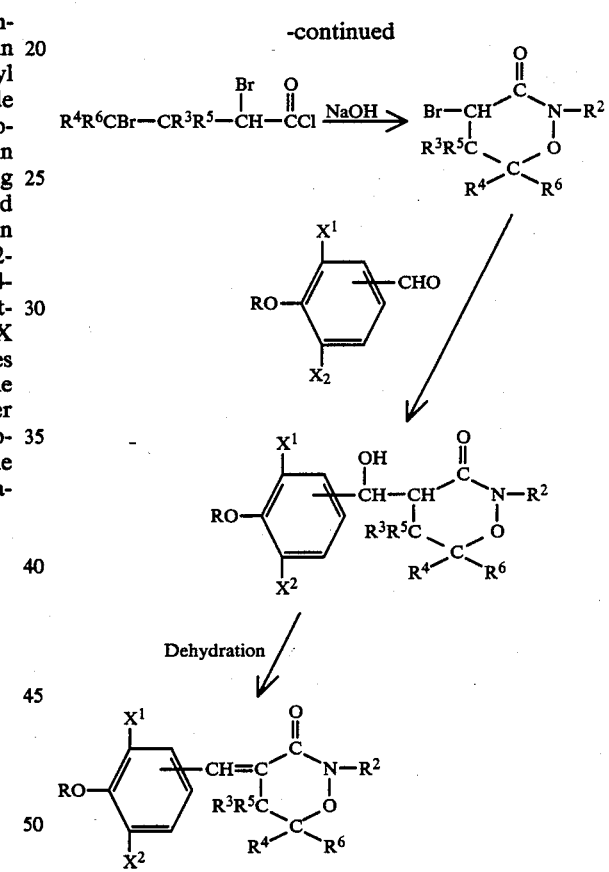

TABLE II

| Ex. | R | R⁴ | R² | R³ | R⁵ | R⁶ | X¹ | X² |
|---|---|---|---|---|---|---|---|---|
| 21 | —COCH₃ | H | —CH₃ | —CH₃ | —CH₃ | H | —C(CH₃)₃ | —C(CH₃)₃ |
| 22 | —COOCH₃ | H | —CH₃ | H | H | —CH₃ | —C(CH₃)₃ | —C(CH₃)₃ |
| 23 | H | —CH₃ | —CH₃ | H | —CH₃ | H | —Si(CH₃)₃ | —Si(CH₃)₃ |
| 24 | —CON(CH₃)₂ | H | —C₂H₅ | —CH₃ | —CH₃ | —CH₃ | —C(CH₃)₃ | —C(CH₃)₃ |
| 25 | H | —CH₂—CH=CH₂ | —CH₃ | H | H | H | —C(CH₃)₃ | —C(CH₃)₃ |
| 26 | —CH₂OCH₃ | H | —CH₃ | H | H | H | —Si(CH₃)₃ | —Si(CH₃)₃ |
| 27 | H | H | H | —CH(CH₂CH₂) (cyclopropyl) | H | H | —C(CH₃)₃ | —C(CH₃)₃ |
| 28 | —COCH₃ | H | —CH₃ | H | H | H | —Si(CH₃)₃ | —Si(CH₃)₃ |

The tetrahydro-3-isoxazepinones of this invention are obtained in a manner similar to that described in the preceding equations except that the alkanoyl chloride reactant in this process is a 2,5-dihaloalkanoyl chloride. This procedure is illustrated by the following equation and Table III which, in combination, illustrate the starting materials and the products obtained thereby:

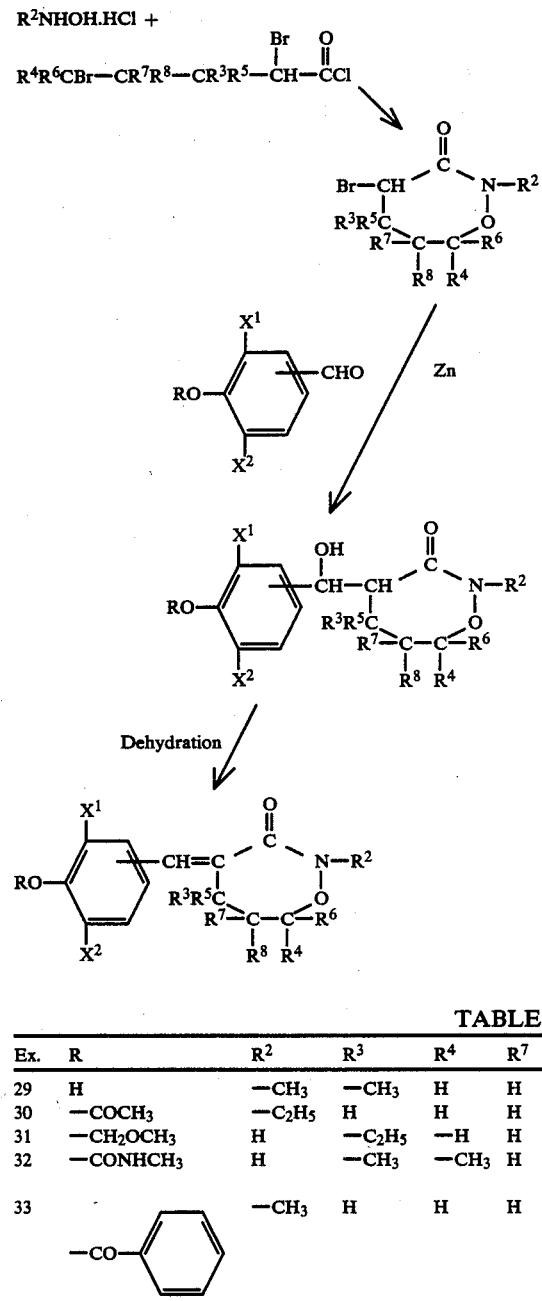

EXAMPLE 35

Dry Filled Capsule

A dry filled capsule is prepared by mixing the following ingredients:

| Ingredient | Mg. Per Capsule |
| --- | --- |
| 4-(3,5-Di-tert-butyl-4-hydroxybenzylidene)-2-methyl-3-isoxazolidinone, E-Isomer | 500 |
| Lactose | 225 |
| Magnesium Stearate | 10 |

The E-isomer of 4-(3,5-di-tert-butyl-4-hydroxybenzylidene)-2-methyl-3-isoxazolidinone is reduced to a No. 60 powder. Lactose and magnesium stearate are passed through a No. 60 bolting cloth onto the powder and the combined ingredients are admixed for ten minutes and filled into a suitable gelatin capsule.

EXAMPLE 36

Compressed Tablet

A compressed tablet suitable for swallowing is prepared by mixing the following ingredients:

| Ingredients | Mg per Tablet |
| --- | --- |
| Dihydro-4-(3,5-di-tert-butyl-4-hydroxybenzylidene)-2-methyl-2H—1,2-oxazin-3(4H)—one | 200 |
| Lactose (U.S. Pat. No. 80 powder) | 100 |
| Cornstarch | 50 |
| Magnesium Stearate | 5 |

The dihydro-4-(3,5-di-tert-butyl-4-hydroxybenzylidene)-2-methyl-2H-1,2-oxazin-3(4H)-one and lactose are mixed thoroughly and granulated with starch paste. The granulated composition is passed through a No. 14 screen while still moist and dried at 45° C. in an oven. When drying is complete the dried material is passed several times through a No. 14 screen and cornstarch is added by passage through a No. 90 bolting cloth. This combination of ingredients is blended and magneisum stearate is added by passage through a No. 60 bolting cloth. The resulting mixture then is blended to a homogeneous mass and pressed into tablets weighing 355 mg per unit.

TABLE III

| Ex. | R | $R^2$ | $R^3$ | $R^4$ | $R^7$ | $R^5$ | $R^6$ | $R^8$ | $X^1$ | $X^2$ |
| --- | --- | --- | --- | --- | --- | --- | --- | --- | --- | --- |
| 29 | H | —CH$_3$ | —CH$_3$ | H | H | —CH$_3$ | H | —CH$_3$ | —C(CH$_3$)$_3$ | —C(CH$_3$)$_3$ |
| 30 | —COCH$_3$ | —C$_2$H$_5$ | H | H | H | H | H | —Si(CH$_3$)$_3$ | —Si(CH$_3$)$_3$ | —Si(CH$_3$)$_3$ |
| 31 | —CH$_2$OCH$_3$ | H | —C$_2$H$_5$ | —H | H | H | —CH$_3$ | H | —C(CH$_3$)$_3$ | —C(CH$_3$)$_3$ |
| 32 | —CONHCH$_3$ | H | —CH$_3$ | —CH$_3$ | H | H | H | H | —C(CH$_3$)$_3$ | —C(CH$_3$)$_3$ |
| 33 | —CO—C$_6$H$_5$ | —CH$_3$ | H | H | H | H | H | —CH$_3$ | —Si(CH$_3$)$_3$ | —Si(CH$_3$)$_3$ |
| 34 | H | —CH$_3$ | H | H | —CH$_3$ | —CH$_3$ | H | —CH$_3$ | —C(CH$_3$)$_3$ | —C(CH$_3$)$_3$ |

The following embodiments illustrate the preparation of typical unit dosage forms, it being understood that other active ingredients, other excipients and other vehicles may be substituted therefore to provide a variety of formulations suitable for oral and/or parenteral administration.

EXAMPLE 37

Oral Liquid

A liquid formulation suitable for oral administration is prepared from the following ingredients:

| Ingredients | |
|---|---|
| Tetrahydro-4-(3,5-di-tert-butyl-4-hydroxy-benzylidene)-2-methyl-3-isoxazepinone | 150 g |
| Sucrose | 200 g |
| Glucose | 100 g |
| Citric Acid | 13 g |
| Sodium Benzoate | 1.0 g |
| Concentrated Orange Oil | 0.2 ml |
| Purified Water, U.S. Pat. (Sufficient to produce | 1000 ml) |

Sucrose and glucose are dissolved in 400 ml of water with heating following which the solution is cooled and citric acid, sodium benzoate and concentrated orange oil are added. The solution is brought to a volume of about 900 ml by the addition of water and tetrahydro-4-(3,5-di-tert-butyl-4-hydroxybenzylidene)-2-methyl-3-isoxazepinone is added. The solution is then filtered and brought to a volume of 1000 ml to provide a liquid suitable for oral administration.

EXAMPLE 38

Adjuvant Arthritis Assay; Developing

This anti-inflammatory study is a modification of the method described by Wong, et al in the Journal of Pharmacology and Experimental Therapeutics, Vol. 185, No. 1; pages 127–138 (1973).

The left and right rear paws of female Lewis rats (Charles River Laboratories) weighing 160–180 grams each were measured by mercury displacement prior to injection (Day Zero).

Adjuvant arthritis was induced in this rat colony by subcutaneous injection of *Mycobacterium butyricum* (0.75 mg in 0.1 ml light mineral oil, Fisher) using an automated Cornwall syringe. On days 11–15 post-adjuvant the injected animals with 0.25 to 0.75 ml. paw edema were selected and distributed evenly, according to edema size, into control and experimental groups of ten rats each. Vehicle control and drug treatments were assigned to the groups at random. The assay was performed using a variable dose level for each test compound per kilogram per day in 0.25% methylcellulose vehicle. All animals were dosed once daily for 4 days and on the fifth day both hind paw volumes were again measured using mercury displacement.

The hind paw edema was determined for each rat by subtracting the hind paw volume measured on Day Zero from the hind paw volume measured on the fifth day of the study. Group means were determined and the drug effect was calculated as percent inhibition of the hind paw edema according to the following equation:

% Inhibition =

$$\frac{(\text{Mean Control Edema} - \text{Mean Experimental Edema})}{\text{Control Edema}} \times 100$$

The results of this study are set forth in Table IV below. The test compounds are identified by reference to the corresponding preparative example, namely, the E & Z Isomers of 4-(3,5-di-tert-butyl-4-hydroxybenzylidene)-2-methyl-3-isoxazolidinone (Example 1) and dihydro-4-(3,5-di-tert-butyl-4-hydroxybenzylidene-2-methyl-2H-1,2-oxazin-3(4H)-one (Example 2). The known anti-inflammatory NAPROXEN was also tested for comparison purposes.

TABLE IV

| Compound | Adjuvant Arthritis ED$_{50}$ (mg/kg) |
|---|---|
| Example 1 (E-Isomer) | 20 |
| Example 1 (Z-Isomer) | 36 |
| Example 2 | 7 |
| NAPROXEN | 28 |

Ulcerogenicity: No gastric or internal lesions were seen when the compounds of Example 1 (E and Z-Isomers) and 2 were administered orally to female Lewis rats once daily for four dys at doses of up to 1000 mg/kg/day. The LD$_{50}$ for the compounds of Example 1 and 2 are greater than 1000 mg/kg.

EXAMPLE 39

Adjuvant Arthritis Assay; Immunomodulatory

Lewis female rats were injected in the tail subcutaneously with *Mycobacterium butyricum* (0.75 mg in 0.1 ml light mineral oil, Fisher) on Day Zero. Prior to injection the volumes of the left and right rear paws were measured by mercury displacement. All rats were dosed orally with vehicle or test compounds on Day 5 to 9 inclusive. The volume of both hind paws were determined on Day 15 and the percent inhibitions were calculated based upon average edema on Day 15 relative to the edema mean in the control group.

TABLE V

| Adjuvant Arthritis Data-Immunomodulatory | | |
|---|---|---|
| Compound | Dosage | % Inhibition |
| Example 1 | 50 mg/kg | 43 |
| Example 2 | 50 mg/kg | 39 |

EXAMPLE 40

Acetylcholine Writhing Assay

Analgesic activity was evaluated via the mouse acetylcholine writhing test using a modification of the procedure described by Collier, et al in Nature (New Biol.) Vol. 204; page 1316 (1964) and Br. J. Pharmacol, Chemother, Vol. 32: page 295 (1968). Each test group consisted of ten male CD-1 mice (Charles River Laboratories) weighing 18–28 grams each. Test compounds suspended in a mixture of 0.25% methylcellulose solution in olive oil were administered orally by gavage and fort five minutes later the mice were injected intraperitoneally with acetylcholine (0.55 mg/ml in 0.25% methylcellulose). The number of writhes in each group of mice were counted for 10 minutes immediately following the injection of acetylcholine and the percent inhibition was calculated as follows:

Inhibition (%) =

$$\left(1 - \frac{\text{Total number of writhes in test group}}{\text{total number of writhes in control group}}\right) \times 100$$

Four dose levels were used to calculate the ED$_{50}$. of each test compounds.

TABLE VI

| Acetylcholine Writhing Assay | |
|---|---|
| Compounds | ED$_{50}$ (Mg/Kg) |
| Example 1 (E-Isomer) | 18 |
| Example 2 | 2.8 |

TABLE VI-continued

| Acetylcholine Writhing Assay | |
|---|---|
| Compounds | $ED_{50}$ (Mg/Kg) |
| NAPROXEN | 6.2 |

EXAMPLE 41

Antipyretic Evaluation

Antipyretic activity was evaluated using a modification of the test described by Loux et al, in Toxicology and Applied Pharmacology, 22:672(1972), that is, yeast-induced fever in rats. Each test group consisted of ten male Sprague-Dawley rats (Charles River Laboratories), weighing 180–225 grams each. Eighteen hours prior to compound administration the rats were weighed and body temperatures were recorded. Food was removed with water available ad libitum.

Each animal was injected subcutaneously into the central dorsal region with five (5.0) ml portions of a 15% (150 mg/1.0 ml) suspension of Fleischman's yeast in distilled water. Eighteen (18) hours after the yeast injection body weights and temperatures were taken and recorded and animals which exhibited an increase in body temperature greater than 1° C. were selected for the study.

Test compounds suspended in 0.25% methylcellulose (0.25% MC) or olive oil were administered orally by gavage nineteen hours following the yeast injection. Body temperatures were taken and recorded one hour after compound administration. Aspirin (300 mg/kg) was the reference standard drug administered with each antipyretic study. The mean temperature of the compound-treated groups, positive control group (Aspirin) and negative control group (vehicle) were calculated at 18 hours and 20 hours. The data was analyzed statistically using a paired-samples Student's t-Test.

TABLE VIII

| Compounds | Change in Temperature (°C.) 18–20 Hour Period[1] |
|---|---|
| 0.25% MC | +0.10 |
| Aspirin (300 mg/kg) | −2.05 |
| Example 1 (300 mg/kg)[2] | −1.33 |
| Example 2 (300 mg/kg)[3] | −1.33 |

[1]All decreases in temperature were significant at $p < 0.05$ using a paired-samples Student's t-Test.
[2]Example 1 was administered in olive oil.
[3]Example 2 was administered in 0.25% methylcellulose.

EXAMPLE 42

Adjuvant Arthritis Assay; Established

Chronic anti-inflammatory and antiarthritic activity were evaluated using the method described by S. Wong in "Tolmetin: A New Non-steroidal Anti-inflammatory Agent" Editor: John R. Ward, Excerpta Medica, N.J. pp. 1–27 (1976). On day 19 post adjuvant all rats were evenly distributed according to edema size. Doses of treatment or vehicle were administered orally to all rats once daily on days 19–22 inclusive. Final paw volumes were determined on day 23 post adjuvant.

TABLE VIII

| Compound | $ED_{50}$ (mg/kg) |
|---|---|
| Example 1 | 44 |
| Example 2 | 8 |
| NAPROXEN | 28 |

What is claimed is:

1. A compound of the formula:

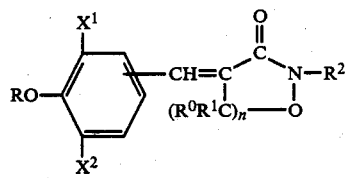

wherein:
R is a member selected from the group consisting of hydrogen, alkyl, alkanoyl, aroyl, alkoxyalkyl, alkoxycarbonyl, lower alkylaminocarbonyl and di-lower alkylaminocarbonyl;
$R^0$, $R^1$ and $R^2$ are the same or different and represent a member selected from the group consisting of hydrogen, lower alkyl, lower alkenyl and lower cycloalkyl:
$X^1$ and $X^2$ are the same or different and represent a member selected from the group consisting of teri-aryalkyl, trimethylsilyl and trifluoromethyl; and
n is an integer having a value of 1–3; and the nontoxic pharmacologically acceptable salts thereof.

2. The compound according to claim 1 wherein R is selected from the group consisting of hydrogen, lower alkanoyl, mononuclear aroyl and lower alkoxyalkyl.

3. The compound according to claim 2 wherein R is selected from the group consisting of hydrogen, acetyl, benzoyl and methoxy lower alkyl.

4. A compound according to claim 1 of the formula:

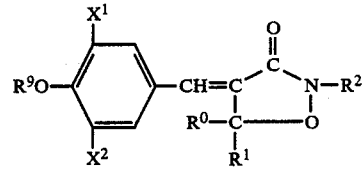

wherein:
$R^9$ is a member selected from the group consisting of hydrogen, alkanoyl and aroyl;
$R^0$, $R^1$ and $R^2$ are the same or different and represent a member selected from the group consisting of hydrogen, lower alkyl, lower alkenyl and lower cycloalkyl;
$X^1$ and $X^2$ are the same or different and represent a member selected from the group consisting of tertiary-lower alkyl and trimethylsilyl; and the nontoxic pharmacologically acceptable salts thereof.

5. The compound according to claim 4 wherein $R^9$ is hydrogen and $X^1$ and $X^2$ are tert-butyl.

6. The compound according to claim 4 wherein $R^9$ is hydrogen; $R^2$ is lower alkyl of 1–4 carbon atoms and $X^1$ and $X^2$ are tert-butyl.

7. The compound according to claim 4 wherein $R^9$ is hydrogen; $R^1$ is hydrogen; $R^2$ is lower alkyl of 1–4 carbon atoms and $X^1$ and $X^2$ are tert-butyl.

8. 4-(3,5-Di-tert-butyl-4-hydroxybenzylidene)-2-methyl-3-isoxazolidinone.

9. The E-isomer of 4-(3,5-di-tert-butyl-4-hydroxybenzylidene)-2-methyl-3-isoxazolidinone.

10. 4-(3,5-Di-tert-butyl-4-hydroxybenzylidene)-2-ethyl-3-isoxazolidinone.

11. 4-(3,5-Di-tert-butyl-4-hydroxybenzylidene)-2-n-propyl-3-isoxazolidinone.

12. 4-(3,5-Di-tert-butyl-4-hydroxybenzylidene)-2,5-dimethyl-3-isoxazolidinone.

13. 4-(3,5-Di-tert-butyl-4-hydroxybenzylidene)-2-isopropyl-3-isoxazolidinone.

14. A compound according to claim 1 of the formula:

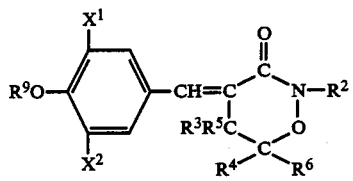

wherein:
$R^9$ is a member selected from the group consisting of hydrogen, alkanoyl and aroyl;
$R^2$–$R^6$ are the same or different and represent a member selected from the group consisting of hydrogen, lower alkyl, lower alkenyl and lower cycloalkyl;
$X^1$ and $X^2$ are the same or different and represent a member selected from the group consisting of tertiary lower alkyl and trimethylsilyl: and the non-toxic pharmacologically acceptable salts thereof.

15. The compound according to claim 14 wherein $R^9$ is hydrogen and $X^1$ and $X^2$ are tert-butyl.

16. The compound according to claim 14 wherein $R^9$ is hydrogen; $R^2$ is lower alkyl of 1–4 carbon atoms and $X^1$ and $X^2$ are tert-butyl.

17. The compound according to claim 14 wherein $R^9$ is hydrogen; $R^2$ is lower alkyl of 1–4 carbon atoms: $R^3$ and $R^4$ are hydrogen and $X^1$ and $X^2$ are tert-butyl.

18. Dihydro-4-(3,5-di-tert-butyl-4-hydroxybenzylidene)-2-methyl-2H-1,2-oxazin-3(4H)-one.

19. Dihydro-4-(3,5-di-tert-butyl-4-hydroxybenzylidene)-2-isopropyl-2H-1,2-oxazin-3(4H)-one.

20. A compound according to claim 1 of the formula:

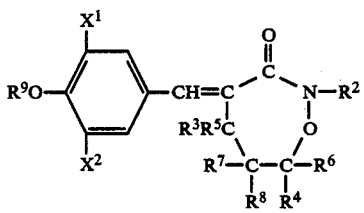

wherein:
$R^9$ is a member selected from the group consisting of hydrogen, alkanoyl and aroyl;
$R^2$–$R^8$ are the same or different and represent a member selected from the group consisting of hydrogen, lower alkyl, lower alkenyl and lower cycloalkyl:
$X^1$ and $X^2$ are the same or different and represent a member selected from the group consisting of tertiaryalkyl and trimethylsilyl; and the non-toxic pharmacologically acceptable salts thereof.

21. The compound according to claim 20 wherein $R^9$ is hydrogen and $X^1$ and $X^2$ are tert-butyl.

22. The compound according to claim 20 wherein $R^9$ is hydrogen; $R^2$ is lower alkyl of 1–4 carbon atoms and $X^1$ and $X^2$ are tert-butyl.

23. Tetrahydro-4-(3,5-di-tert-butyl-4-hydroxybenzylidene)-2-methyl-3-isoxazepinone.

24. A pharmaceutical composition comprising as an active ingredient a compound of the formula:

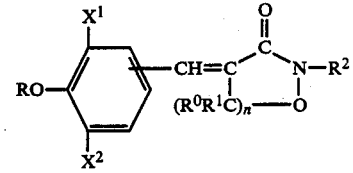

wherein:
R is a member selected from the group consisting of hydrogen, alkyl, alkanoyl, aroyl, alkoxyalkyl, alkoxycarbonyl, lower alkylaminocarbonyl and di-lower alkylaminocarbonyl;
$R^0$, $R^1$ and $R^2$ are the same or different and represent a member selected from the group consisting of hydrogen, lower alkyl, lower alkenyl and lower cycloalkyl;
$X^1$ and $X^2$ are the same or different and represent a member selected from the group consisting of tertiary-alkyl, trimethylsilyl and trifluoromethyl; and
n is an integer having a value of 1–3; or a non-toxic pharmacologically acceptable salt thereof; and a pharmaceutically acceptable carrier.

25. A pharmaceutical composition according to claim 24 wherein the active ingredient is a compound in which R is selected from the group consisting of hydrogen, acetyl, benzoyl and methoxy lower alkyl.

26. A pharmaceutical composition according to claim 24 wherein the active ingredient is a compound of the formula:

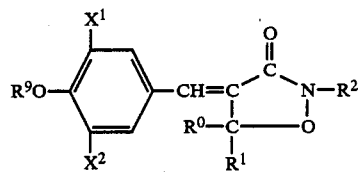

wherein:
$R^9$ is a member selected from the group consisting of hydrogen, alkanoyl and aroyl;
$R^0$, $R^1$ and $R^2$ are the same or different and represent a member selected from the group consisting of hydrogen, lower alkyl, lower alkenyl and lower cycloalkyl;
$X^1$ and $X^2$ are the same or different and represent a member selected from the group consisting of tertiary lower alkyl and trimethylsilyl: or a non-toxic pharmacologically acceptable salt thereof; and a pharmaceutically acceptable carrier.

27. A pharmaceutical composition according to claim 26 wherein the active ingredient is 4-(3,5-di-tert-butyl-4-hydroxybenzylidene)-2-methyl-3-isoxazolidinone.

28. A pharmaceutical composition according to claim 26 wherein the active ingredient is the E-isomer of 4-(3,5-di-tert-butyl-4-hydroxybenzylidene)-2-methyl-3-isoxazolidinone.

29. A pharmaceutical composition according to claim 24 wherein the active ingredient is a compound of the formula:

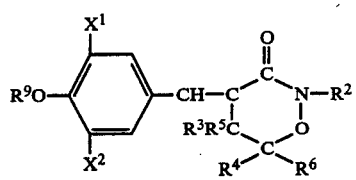

wherein:
R⁹ is a member selected from the group consisting of hydrogen, alkanoyl and aroyl;
R²–R⁶ are the same or different and represent a member selected from the group consisting of hydrogen, lower alkyl, lower alkenyl and lower cycloalkyl;
X¹ and X² are the same or different and represent a member selected from the group consisting of tertiary-lower alkyl and trimethylsilyl; or a non-toxic pharmacologically acceptable salt thereof.

30. A pharmaceutical composition according to claim 24 wherein the active ingredient is dihydro-4-(3,5-di-tert-butyl-4-hydroxy-benzylidene)-2-methyl-2H-1,2-oxazin-3(4H)-one.

31. A pharmaceutical composition according to claim 24 wherein the active ingredient is a compound of the formula:

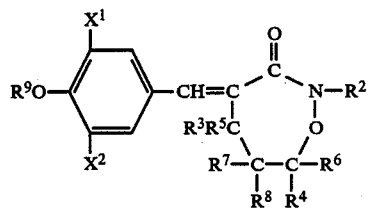

wherein:
R⁹ is a member selected from the group consisting of hydrogen, alkanoyl and aroyl:
R²–R⁸ are the same or different and represent a member selected from the group consisting of hydrogen, lower alkyl, lower alkenyl and lower cycloalkyl;
X¹ and X² are the same or different and represent a member selected from the group consisting of tertiaryalkyl and trimethylsilyl: or a non-toxic pharmacologically acceptable acid addition salt thereof.

32. A method for treating inflammation in a mammal which comprises administering a safe and effective amount of a compound having the formula:

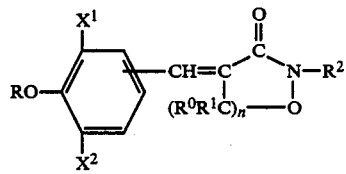

wherein:
R is a member selected from the group consisting of hydrogen, alkyl, alkanoyl, aroyl, alkoxyalkyl, alkoxycarbonyl, lower alkylaminocarbonyl and dilower alkylaminocarbonyl;
R⁰, R¹ and R² are the same or different and represent a member selected from the group consisting of hydrogen, lower alkyl, lower alkenyl and lower cycloalkyl;
X¹ and X² are the same or different and represent a member selected from the group consisting of tertiaryalkyl, trimethylsilyl and trifluoromethyl; and
n is an integer having a value of 1–3; or a non-toxic pharmacologically acceptable salt thereof.

33. A method according to claim 32 wherein the active ingredient is administered orally.

34. A method according to claim 32 wherein the active ingredient is a compound in which R is selected from the group consisting of hydrogen, acetyl, benzoyl and methoxy lower alkyl.

35. A method according to claim 32 wherein the active ingredient is a compound of the formula:

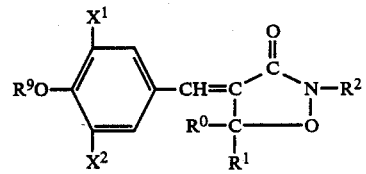

wherein:
R⁹ is a member selected from the group consisting of hydrogen, alkanoyl and aroyl;
R⁰, R¹ and R² are the same or different and represent a member selected from the group consisting of hydrogen, lower alkyl, lower alkenyl and lower cycloalkyl;
IX¹ and X² are the same or different and represent a member selected from the group consisting of tertiary lower alkyl and trimethylsilyl: or a non-toxic pharmacologically acceptable salt thereof.

36. A method according to claim 35 wherein the active ingredient is 4-(3,5-di-tert-butyl-4-hydroxybenzylidene)-2-methyl-3-isoxazolidinone.

37. A method according to claim 35 wherein the active ingredient is the E-isomer of 4-(3,5-di-tert-butyl-4-hydroxybenzylidene)-2-methyl-3-isoxazolidinone.

38. A method according to claim 32 wherein the active ingredient is a compound of the formula:

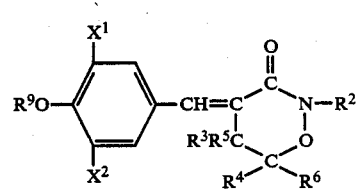

wherein:
R⁹ is a member selected from the group consisting of hydrogen, alkanoyl and aroyl;
R²–R⁶ are the same or different and represent a member selected from the group consisting of hydrogen, lower alkyl, lower alkenyl and lower cycloalkyl;
X¹ and X² are the same or different and represent a member selected from the group consisting of tertiary lower alkyl and trimethylsilyl: or a non-toxic pharmacologically acceptable salt thereof.

39. A method according to claim 38 wherein the active ingredient is dihydro-4-(3,5-di-tert-butyl-4-hydroxybenzylidene)-2-methyl-2H-1,2-oxazin-3(4H)-one.

40. A method according to claim 32 wherein the active ingredient is a compound of the formula:

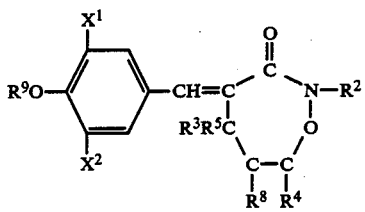

wherein:
  $R^9$ is a member selected from the group consisting of hydrogen, alkanoyl and aroyl;
  $R^2$–$R^8$ are the same or different and represent a member selected from the group consisting of hydrogen, lower alkyl, lower alkenyl and lower cycloalkyl;
  $X^1$ and $X^2$ are the same or different and represent a member selected from the group consisting of tertiaryalkyl and trimethylsilyl; or a non-toxic pharmacologically acceptable salt thereof.

41. A compound of the formula:

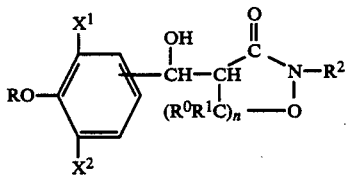

wherein:
  R is a member selected from the group consisting of hydrogen, alkyl, alkanoyl, aroyl, alkoxyalkyl, alkoxycarbonyl, lower alkylaminocarbonyl and di-lower alkylaminocarbonyl.
  $R^0$, $R^1$ and $R^2$ are the same or different and represent a member selected from the group consisting of hydrogen, lower alkyl, lower alkenyl and lower cycloalkyl;
  $X^1$ and $X^2$ are the same or different and represent a member selected from the group consisting of teriaryalkyl, trimethylsilyl and trifluoromethyl; and
  n is an integer having a value of 1–3; and the nontoxic pharmacologically acceptable salts thereof.

42. A compound according to claim 41 of the formula:

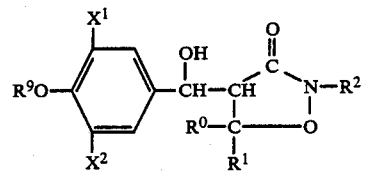

wherein:
  $R^9$ is a member selected from the group consisting of hydrogen, alkanoyl and aroyl;
  $R^0$, $R^1$ and $R^2$ are the same or different and represent a member selected from the group consisting of hydrogen, lower alkyl, lower alkenyl and lower cycloalkyl;
  $X^1$ and $X^2$ are the same or different and represent a member selected from the group consisting of tertiary lower alkyl and trimethylsilyl; and the nontoxic pharmacologically acceptable salts thereof.

43. A compound according to claim 41 of the formula:

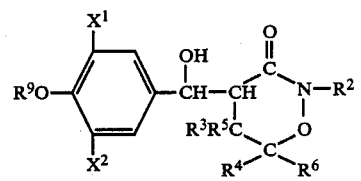

wherein:
  $R^9$ is a member selected from the group consisting of hydrogen, alkanoyl and aroyl;
  $R^2$–$R^6$ are the same or different and represent a member selected from the group consisting of hydrogen, lower alkyl, lower alkenyl and lower cycloalkyl;
  $X^1$ and $X^2$ are the same or different and represent a member selected from the group consisting of tertiary-lower alkyl and trimethylsilyl; and the non-toxic pharmacologically acceptable salts thereof.

44. A compound according to claim 41 of the formula:

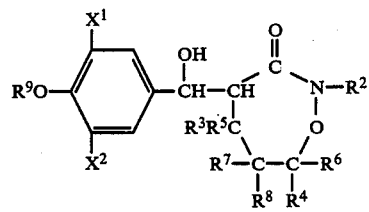

wherein:
  $R^9$ is a member selected from the group consisting of hydrogen, alkanoyl and aroyl;
  $R^2$–$R^8$ are the same or different and represent a member selected from the group consisting of hydrogen, lower alkyl, lower alkenyl and lower cycloalkyl;
  $X^1$ and $X^2$ are the same or different and represent a member selected from the group consisting of tertiaryalkyl and trimethylsilyl; and the non-toxic pharmacologically acceptable salts thereof.

* * * * *